(12) United States Patent
Jones et al.

(10) Patent No.: US 11,147,936 B2
(45) Date of Patent: Oct. 19, 2021

(54) DOSE DELIVERY DEVICE WITH COVER CONNECTED TO DOSE CHAMBER SEAL

(71) Applicant: MANTA DEVICES, LLC, Cambridge, MA (US)

(72) Inventors: Andrew Jones, Roslindale, MA (US); Richard L. Miller, Needham, MA (US)

(73) Assignee: MANTA DEVICES, LLC, Cambridge, MA (US)

( * ) Notice: Subject to any disclaimer, the term of this patent is extended or adjusted under 35 U.S.C. 154(b) by 1107 days.

(21) Appl. No.: 15/308,511

(22) PCT Filed: May 1, 2015

(86) PCT No.: PCT/US2015/028816
§ 371 (c)(1),
(2) Date: Nov. 2, 2016

(87) PCT Pub. No.: WO2015/168572
PCT Pub. Date: Nov. 5, 2015

(65) Prior Publication Data
US 2017/0119982 A1 May 4, 2017

Related U.S. Application Data

(60) Provisional application No. 61/987,662, filed on May 2, 2014.

(51) Int. Cl.
*A61M 15/00* (2006.01)
*A61M 11/08* (2006.01)

(52) U.S. Cl.
CPC ........ *A61M 15/0043* (2014.02); *A61M 11/08* (2013.01); *A61M 15/0025* (2014.02);
(Continued)

(58) Field of Classification Search
CPC .......... A61M 15/0025; A61M 15/0028; A61M 15/0033; A61M 15/0035; A61M 15/0036;
(Continued)

(56) References Cited

U.S. PATENT DOCUMENTS 1,410,556 A   3/1922   Dorment
2,307,986 A   1/1943   Bolte et al.
(Continued)

FOREIGN PATENT DOCUMENTS

CA   1329083 C   5/1994
DE   4400083 A1  7/1995
(Continued)

OTHER PUBLICATIONS

International Search Report and Written Opinion dated Oct. 23, 2015 in corresponding PCT Patent Application No. PCT/US 15/28816, 11pgs.
(Continued)

*Primary Examiner* — Kathryn E Ditmer
(74) *Attorney, Agent, or Firm* — Grossman, Tucker, Perrault & Pfleger, PLLC

(57) ABSTRACT

Dose delivery device with partially or fully surrounding cover may be removed to open fluid communication with a dose chamber. The cover may allow an inhaler to be stored in sterile or otherwise in a controlled environment prior to use, and removal of the cover may automatically prepare the inhaler for use.

13 Claims, 18 Drawing Sheets

(52) U.S. Cl.
CPC ..... *A61M 15/0028* (2013.01); *A61M 15/0003* (2014.02); *A61M 2202/06* (2013.01); *A61M 2202/064* (2013.01); *A61M 2205/6054* (2013.01); *A61M 2206/16* (2013.01); *A61M 2209/06* (2013.01)

(58) Field of Classification Search
CPC ............ A61M 15/0038; A61M 15/004; A61M 15/0041; A61M 15/0043; A61M 2209/06; A61B 2050/005; A61B 2050/0065; B65D 51/185; B65D 51/20; B65D 51/22
See application file for complete search history.

(56) References Cited

U.S. PATENT DOCUMENTS

| | | |
|---|---|---|
| 2,436,878 A | 3/1948 | Biederman |
| 2,590,832 A | 3/1952 | Brown |
| 2,603,216 A | 7/1952 | Taplin et al. |
| 2,701,053 A * | 2/1955 | Tamarin ................. B65D 75/66 221/32 |
| 2,860,638 A | 11/1958 | Bartolomeo |
| 2,974,787 A | 3/1961 | Cooper |
| 3,172,405 A | 3/1965 | Sugg |
| 3,888,253 A | 6/1975 | Watt et al. |
| 2,893,392 A | 6/1976 | Gerstel et al. |
| 4,064,878 A | 12/1977 | Lundquist |
| 4,104,027 A | 8/1978 | Lundquist |
| 4,249,526 A | 2/1981 | Dean et al. |
| 4,338,931 A | 7/1982 | Cavazza |
| 4,601,896 A | 7/1986 | Nugent |
| 4,782,967 A * | 11/1988 | Thomas ................. B65D 51/20 206/532 |
| 4,811,731 A * | 3/1989 | Newell ............. A61M 15/0045 128/203.15 |
| 4,841,964 A | 6/1989 | Hurka et al. |
| 4,860,740 A * | 8/1989 | Kirk ................. A61M 15/0028 128/203.15 |
| 5,035,237 A | 7/1991 | Newell et al. |
| 5,108,003 A * | 4/1992 | Granofsky .......... B65D 17/506 220/257.2 |
| 5,167,242 A | 12/1992 | Turner et al. |
| 5,239,992 A | 8/1993 | Bougamont et al. |
| 5,239,993 A | 8/1993 | Evans |
| 5,320,714 A | 6/1994 | Brendel |
| 5,337,740 A | 8/1994 | Armstrong |
| 5,388,572 A | 2/1995 | Mulhauser et al. |
| 5,400,808 A | 3/1995 | Turner et al. |
| 5,447,151 A | 9/1995 | Bruna et al. |
| 5,476,093 A | 12/1995 | Lankinen |
| 5,483,954 A | 1/1996 | Mecikalski |
| 5,484,101 A * | 1/1996 | Hedberg ................. B65D 5/708 220/255 |
| 5,501,236 A | 3/1996 | Hill et al. |
| 5,529,059 A | 6/1996 | Armstrong et al. |
| 5,533,502 A | 7/1996 | Piper |
| 5,533,505 A * | 7/1996 | Kallstrand ......... A61M 15/0028 128/203.15 |
| 5,562,918 A | 10/1996 | Stimpson |
| 5,596,982 A | 1/1997 | Blaha-Schnabel |
| 5,622,166 A | 4/1997 | Eisele et al. |
| 5,647,349 A | 7/1997 | Ohki et al. |
| 5,669,378 A | 9/1997 | Pera et al. |
| 5,673,793 A | 10/1997 | Seidler |
| 5,687,710 A | 11/1997 | Ambrosio et al. |
| 5,694,920 A | 12/1997 | Abrams et al. |
| 5,715,810 A | 2/1998 | Armstrong et al. |
| 5,893,452 A | 4/1999 | De Nervo |
| 5,921,237 A | 7/1999 | Eisele et al. |
| 5,947,117 A | 9/1999 | Herold |
| 5,954,204 A | 9/1999 | Grabowski |
| 6,029,663 A | 2/2000 | Eisele et al. |
| 6,082,568 A * | 7/2000 | Flanagan ............. B65D 51/20 215/232 |
| 6,089,228 A | 7/2000 | Smith et al. |
| 6,102,035 A | 8/2000 | Asking et al. |
| 6,209,538 B1 | 4/2001 | Casper et al. |
| 6,230,707 B1 | 5/2001 | Horlin |
| 6,234,169 B1 | 5/2001 | Bulbrook et al. |
| 6,328,034 B1 | 12/2001 | Eisele et al. |
| 6,347,629 B1 | 2/2002 | Braithwaite |
| 6,401,712 B1 | 6/2002 | Von Schuelanann |
| 6,427,688 B1 | 8/2002 | Ligotke et al. |
| 6,443,152 B1 | 9/2002 | Lockhart et al. |
| 6,443,307 B1 | 9/2002 | Burridge |
| 6,536,427 B2 | 3/2003 | Davies et al. |
| 6,550,477 B1 | 4/2003 | Casper et al. |
| 6,561,186 B2 | 5/2003 | Casper et al. |
| 6,595,203 B1 | 7/2003 | Bird |
| 6,595,210 B2 | 7/2003 | Ohki et al. |
| 6,606,992 B1 | 8/2003 | Schuler et al. |
| 6,655,381 B2 | 12/2003 | Keane et al. |
| 6,681,768 B2 | 1/2004 | Haaije De Boer et al. |
| 6,722,364 B2 | 4/2004 | Connelly et al. |
| 6,725,857 B2 | 4/2004 | Ritsche |
| 6,748,947 B2 | 6/2004 | Keane et al. |
| 6,810,872 B1 | 11/2004 | Ohki et al. |
| 6,810,873 B1 | 11/2004 | Haikarainen et al. |
| 6,871,646 B2 | 3/2005 | Keane et al. |
| 6,880,555 B1 | 4/2005 | Brunnberg et al. |
| 6,929,004 B1 * | 8/2005 | Bonney ............ A61M 15/0028 128/203.15 |
| 6,932,082 B2 | 8/2005 | Stein |
| 6,941,947 B2 | 9/2005 | Young et al. |
| 6,971,384 B2 | 12/2005 | Gieschen et al. |
| 7,025,056 B2 | 4/2006 | Eason et al. |
| 7,025,057 B2 | 4/2006 | Chawla |
| 7,143,765 B2 | 12/2006 | Asking et al. |
| 7,305,986 B1 | 12/2007 | Steiner et al. |
| 7,401,713 B2 | 7/2008 | Ede et al. |
| 7,533,668 B1 * | 5/2009 | Widerstrom ....... A61M 15/0028 128/203.12 |
| 7,540,383 B2 * | 6/2009 | Hutter .................. B65D 75/327 206/530 |
| 7,617,822 B2 | 11/2009 | De Boer et al. |
| 8,109,267 B2 | 2/2012 | Villax et al. |
| 8,156,936 B2 | 4/2012 | Steiner et al. |
| 8,250,982 B2 * | 8/2012 | Kothe ..................... F42C 15/20 102/336 |
| 8,261,739 B2 | 9/2012 | Harris et al. |
| 8,590,531 B2 | 11/2013 | Rouse et al. |
| 8,671,937 B2 | 3/2014 | Steiner et al. |
| 9,125,998 B2 | 9/2015 | Harmer et al. |
| 2001/0020472 A1 | 9/2001 | Horlin |
| 2001/0029948 A1 | 10/2001 | Ingle et al. |
| 2002/0006316 A1 | 1/2002 | Schuler et al. |
| 2002/0020408 A1 | 2/2002 | Knauer |
| 2002/0048552 A1 * | 4/2002 | Garrill .................. A61M 15/00 424/45 |
| 2002/0092523 A1 | 7/2002 | Connelly et al. |
| 2002/0092524 A1 | 7/2002 | Lockhart et al. |
| 2002/0108611 A1 * | 8/2002 | Johnston ........... A61M 15/0028 128/203.15 |
| 2002/0170560 A1 | 11/2002 | Young et al. |
| 2003/0034271 A1 | 2/2003 | Burridge |
| 2003/0192532 A1 | 10/2003 | Hopkins |
| 2004/0118399 A1 | 6/2004 | Young et al. |
| 2004/0182387 A1 | 9/2004 | Steiner et al. |
| 2004/0206350 A1 | 10/2004 | Alston et al. |
| 2004/0206773 A1 | 10/2004 | Ede et al. |
| 2004/0211419 A1 | 10/2004 | Eason et al. |
| 2004/0236282 A1 | 11/2004 | Braithwaite |
| 2005/0022813 A1 | 2/2005 | Alston |
| 2005/0056281 A1 | 3/2005 | Snow |
| 2005/0172964 A1 * | 8/2005 | Anderson ............... A61J 1/035 128/203.21 |
| 2005/0188988 A1 | 9/2005 | Poole et al. |
| 2005/0238708 A1 | 10/2005 | Jones et al. |
| 2005/0284473 A1 * | 12/2005 | Young ............. A61M 15/0028 128/203.15 |
| 2006/0005833 A1 | 1/2006 | Gieschen et al. |
| 2006/0062740 A1 | 3/2006 | Rand |

(56) References Cited

U.S. PATENT DOCUMENTS

| | | |
|---|---|---|
| 2006/0108877 A1 | 5/2006 | Tegel |
| 2006/0138016 A1 | 6/2006 | Harper |
| 2006/0157053 A1 | 7/2006 | Barney et al. |
| 2006/0169278 A1 | 8/2006 | Djupesland et al. |
| 2006/0169280 A1 | 8/2006 | Yama et al. |
| 2006/0237010 A1* | 10/2006 | De Boer ............ A61M 15/0045 128/203.15 |
| 2007/0023381 A1 | 2/2007 | Ceryeny |
| 2007/0074721 A1 | 4/2007 | Harmer et al. |
| 2007/0151562 A1 | 7/2007 | Jones et al. |
| 2008/0190424 A1* | 8/2008 | Lucking ................ A61K 9/0075 128/203.15 |
| 2008/0251072 A1 | 10/2008 | Lulla et al. |
| 2008/0314384 A1 | 12/2008 | Harris et al. |
| 2009/0084379 A1* | 4/2009 | Goeckner .......... A61M 15/0028 128/203.15 |
| 2009/0090362 A1 | 4/2009 | Harmer et al. |
| 2009/0114220 A1 | 5/2009 | Wachtel et al. |
| 2009/0139888 A1* | 6/2009 | Berry ................. B65D 73/0057 206/438 |
| 2009/0250057 A1 | 10/2009 | Wachtel |
| 2009/0250058 A1* | 10/2009 | Lastow ............. A61M 15/0028 128/203.15 |
| 2009/0308392 A1 | 12/2009 | Smutney et al. |
| 2009/0321129 A1 | 12/2009 | Ede et al. |
| 2010/0059052 A1* | 3/2010 | Davies ..................... A61J 1/035 128/203.15 |
| 2010/0154795 A1* | 6/2010 | Pentafragas ...... A61M 15/0028 128/203.15 |
| 2012/0043323 A1* | 2/2012 | Thomas .................... B65D 5/38 220/254.1 |
| 2013/0032145 A1* | 2/2013 | Adler ................ A61M 15/0028 128/203.15 |
| 2013/0042864 A1* | 2/2013 | Adler ................ A61M 15/0028 128/203.15 |
| 2013/0061851 A1 | 3/2013 | Jones et al. |
| 2013/0239964 A1* | 9/2013 | Young ............... A61M 15/0028 128/203.21 |
| 2013/0312747 A1 | 11/2013 | Eason et al. |
| 2014/0083423 A1* | 3/2014 | Jung ................. A61M 15/0028 128/203.21 |
| 2014/0102451 A1 | 4/2014 | Jones et al. |
| 2014/0230817 A1* | 8/2014 | Richardson ....... A61M 15/0028 128/203.15 |
| 2014/0290654 A1 | 10/2014 | Poole et al. |

FOREIGN PATENT DOCUMENTS

| | | |
|---|---|---|
| EP | 0407276 A2 | 1/1991 |
| GB | 1211168 A | 11/1967 |
| GB | 2179260 | 3/1987 |
| GB | 2375310 A | 11/2002 |
| GB | 2405798 A | 3/2005 |
| JP | H08103499 A | 4/1996 |
| JP | 2002165884 A | 6/2002 |
| JP | 2004008697 A | 1/2004 |
| WO | 9007351 A1 | 7/1990 |
| WO | 9204928 A2 | 4/1992 |
| WO | WO 96/09085 | 3/1996 |
| WO | WO 99/06092 A1 | 2/1999 |
| WO | WO 01/05675 A1 | 1/2001 |
| WO | WO 01/26720 A1 | 4/2001 |
| WO | WO01-56640 | 8/2001 |
| WO | WO 01/85097 | 11/2001 |
| WO | WO02-00280 | 1/2002 |
| WO | WO 02/098495 A1 | 12/2002 |
| WO | WO 03/000326 A1 | 1/2003 |
| WO | WO 03/015857 A1 | 2/2003 |
| WO | 2004103446 A1 | 12/2004 |
| WO | WO 2005/002654 A3 | 1/2005 |
| WO | WO 2005/025656 A1 | 3/2005 |
| WO | 2005037353 A1 | 4/2005 |
| WO | WO 2005/030305 A1 | 4/2005 |
| WO | 2006090149 A2 | 8/2006 |
| WO | 2007068896 A1 | 6/2007 |
| WO | 2010021589 A1 | 2/2010 |
| WO | WO-2010021589 A1 * | 2/2010 ........ A61M 15/0028 |
| WO | 2013036881 A2 | 3/2013 |
| WO | WO2013036881 | 3/2013 |
| WO | WO-2013036881 A2 * | 3/2013 ........ A61M 15/0028 |
| WO | WO-2015097034 A1 * | 7/2015 |

OTHER PUBLICATIONS

English language EP Search Report dated Mar. 30, 2017, received in related EP Application No. 05812327.4, 7 pgs.

PCT International Preliminary Report on Patentability dated Jul. 19, 2011, received in related PCT Application No. PCT/US10/00090, 10 pgs.

English language EPO Search Report dated Sep. 23, 2015, received in related EP Application No. 15150445.3, 5 pgs.

JP Office Action with English Translation, dated Nov. 25, 2015, received in related JP Application No. 2014-231220, 11 pgs.

JP Office Action with English Translation, dated Feb. 26, 2014, received in related JP Application No. 2013-021615, 4 pgs.

PCT International Search Report dated Feb. 23, 2009, received in related PCT Application No. PCT/US08/08303, 5 pgs.

English language EP Search Report dated Oct. 23, 2015, received in related EP Application No. 14198194.4, 6 pgs.

U.S. Office Action dated Nov. 1, 2016, received in related U.S. Appl. No. 14/248,628, 31 pgs.

Examination Report dated Sep. 7, 2017, received in India Application No. 709/DELNP/2010, with English language translations included, 6 pgs.

European Communication dated Feb. 12, 2019 along with extended European Search Report completed Jan. 31, 2019 in connection with European Patent Application No. 18178534.6.

Extended European Search Report, dated Dec. 19, 2017, in related EP Application No. 15785580.0, 8 pages.

Office Action, dated Feb. 8, 2018, in related EP Application No. 14198194.4, 7 pages.

Indian Office Action dated Mar. 5, 2021 in corresponding Indian Patent Application No. 201818021046.

* cited by examiner

_US 11,147,936 B2_

DOSE DELIVERY DEVICE WITH COVER CONNECTED TO DOSE CHAMBER SEAL

CROSS-REFERENCE TO RELATED APPLICATIONS

This application claims the benefit of U.S. Provisional Patent Application Ser. No. 61/987,662, filed on May 2, 2014, which is fully incorporated herein by reference.

TECHNICAL FIELD

The present disclosure relates to medicament delivery devices and more particularly, to a dose delivery device for delivering a dose of medicament via inhalation.

BACKGROUND INFORMATION

Medicament in the form of dry powder may be delivered directly into the nasal cavity or lungs, such as by inhalation. Administering medicament in this manner may prove less invasive than other drug delivery techniques, such as hypodermic injections. Direct inhalation of medicament may also allow smaller doses to be used to achieve results similar to those of the same drug taken orally. Successful inhalation therapies require robust patient compliance.

SUMMARY

Aspects of the invention relate to devices, systems, and methods that are used to deliver a dose of a powder or fluid, such as a vaccine, a vitamin, a flavorant, or other medicament or substance. The devices, systems and methods may include features that allow the device to be protected (e.g., from contamination and/or degradation) prior to use, and minimize the steps of use required by the user to handle and prepare the device for inhalation. For example, in some embodiments, the dose is isolated to a selected volume/dose chamber by a barrier, such as a sealing material across an opening of the dose chamber, and the sealing material may be attached to an external cover that protects the entire delivery device and prevents the ingress of contaminants prior to use. Prior to use, the user may open the external cover and remove the device causing the sealing material to separate from the device. As a result, the user may withdraw the device from the cover in a predictable manner, simultaneously removing the dose chamber sealing material, and the device is ready for inhalation without additional steps of preparation.

Accordingly, aspects of the invention may provide an improved dry powder inhaler that increases patient compliance by simplifying the user steps of use, ensures that the inhaler is properly prepared for inhalation and allows the sterile handling of the device prior to the inhalation maneuver. In some embodiments, the dry powder inhaler includes a mouthpiece, dose chamber and a cover that is simple to open, presents a handle for holding the device and automatically opens the dose chamber upon removal of the cover. This inhaler design has significant advantages for ease of use, patient compliance, sterile handling in non-sterile environments and quick access in emergency/rescue situations.

In one aspect of the invention, a dose delivery device may include a mouthpiece, a dose chamber and a cap with an integral opening mechanism. The mouthpiece may have an air path with an inlet and an outlet, and may be attached to the dose chamber that stores a dose which may be delivered to a subject via the mouthpiece as the user inhales. The cap may surround or cover at least a portion of the mouthpiece, and when the cap is removed from the mouthpiece, the opening mechanism may open a sealing mechanism that seals the dose chamber while the inhaler is in its stored state. Opening of the sealing mechanism may permit the release of dose from the dose chamber to the air path of the mouthpiece. Furthermore, the cap may engage with the mouthpiece such that the cap acts as a guide to control the separation of the sealing material from the dose chamber during the cover removal. In one embodiment, the engaging geometry of the cap and mouthpiece may guide movement of the cap during removal that suitably causes the sealing mechanism to open the dose chamber. For example, the sealing mechanism may include a layer of barrier material that is positioned over an opening of the dose chamber. To remove the cap from the mouthpiece, the cap may need to be moved linearly, as guided by engagement with the mouthpiece, which causes linear movement of the barrier material relative to the dose chamber. Thus, the barrier material may be slidably removed from the dose chamber, opening the dose chamber fluid communication with the mouthpiece.

The cap or other cover may be positioned over the mouthpiece outlet to provide protection for and/or provide a sterile or otherwise clean environment for the mouthpiece, and may provide other functions. In some embodiments, positioning the cover over the mouthpiece may locate the sealing mechanism, e.g., a layer of barrier material, relative to the dose chamber. That is, the cover may be attached to the barrier material, and positioning of the cover on the mouthpiece may properly position the barrier material to close the dose chamber when the dose-filled dose chamber is attached to the mouthpiece and sealed against the barrier material. Thus, the barrier material may block fluid communication between the dose chamber and the air path until the cover is removed from the mouthpiece, thereby removing the barrier material from engagement with the dose chamber.

In some embodiments, portions of the inhaler body may provide grip surfaces to facilitate handling of the inhaler by a user. For example, a handle may extend from the mouthpiece in a way that the user can grip the handle and hold the device for use.

In some embodiments, the cover may completely surround the mouthpiece and dose chamber. For example, a layer of barrier material, e.g., foil packaging, may surround the inhaler assembly and be arranged such that removal of the cover opens fluid communication between the dose chamber and air path, e.g., by removing a sealing mechanism from the dose chamber.

In another aspect of the invention, a dose delivery device includes an inhaler assembly including a mouthpiece and a dose chamber. The mouthpiece may have an air path with at least one inlet and an outlet, and be attached to a dose chamber that stores a dose to be delivered to a subject via the mouthpiece outlet during an inhalation maneuver. The device may also include a sealing material that seals the dose chamber when the dose chamber is mounted to the mouthpiece. For example, when the dose chamber is mounted to the mouthpiece, the sealing material may be captured between the mouthpiece and the dose chamber to prevent fluid communication between the two and confining the dose to the dose chamber. A cover, e.g., including an external barrier layer material such as a foil packaging, may surround the mouthpiece and dose chamber and is attached to the sealing material such that opening and separating the inhaler assembly from the cover opens fluid communication between the dose chamber and the air path.

In another aspect of the invention, a dose delivery device includes an inhaler assembly including a mouthpiece, a dose chamber and a sealing mechanism. The mouthpiece may engage with the sealing mechanism to position the sealing mechanism during assembly and/or to guide movement of the sealing mechanism relative to the dose chamber to open the fluid communication between the dose chamber and the mouthpiece for dose delivery.

In another aspect of the invention, a dose delivery device includes an inhaler assembly that includes a mouthpiece, a dose chamber and an external package. The external package may integrate a sealing mechanism to seal the dose chamber when the inhaler is in its stored state, e.g., a portion of the external package may be positioned between the dose chamber and a portion of the mouthpiece to prevent fluid communication between the dose chamber and the mouthpiece outlet. However, removal of the external package may automatically open fluid communication between the dose chamber and the mouthpiece. In other embodiments, the sealing mechanism may engage the dose chamber or the mouthpiece to prevent fluid communication between the two.

Aspects of the invention can be used in any suitable arrangement, including dose delivery devices that are usable a single time with a single dose chamber, and including a dose delivery device that is usable multiple times with multiple dose chambers. For example, dose delivery device may include a plurality of dose chambers arranged in a multi-dose chamber configuration in which each dose chamber can be serially opened and used to deliver a dose to a user. In other arrangements, two or more dose chambers may be opened for combination product delivery, e.g., simultaneous delivery.

In another aspect of the invention, a dose delivery device comprises a body including a mouthpiece having an outlet, e.g., for delivery of dose to a user by inhalation. The body may also define a flow path that extends from an inlet to the outlet. The flow path may be straight or linear, or may include curved or other non-linear sections. A dose chamber containing a dose to be delivered to a subject via the mouthpiece may be engaged with the body, and a seal may close fluid communication between the flow path and the dose chamber. For example, the seal may include a layer of barrier material that is sandwiched between the dose chamber and the body, that is attached to the dose chamber, that is attached to a portion of the body, or is otherwise arranged to resist fluid communication between the dose chamber and the flow path. A cover may at least partially cover a portion of the body, such as a portion of the mouthpiece at the outlet or may completely surround the body and the dose chamber. The cover may be connected to the seal such that removal of the cover from the portion of the body covered by the cover causes the seal to open fluid communication between the flow path and the dose chamber. For example, a layer of barrier material that functions as the seal may be attached to the cover and pulled from engagement with the dose chamber and/or body to open fluid communication when the cover is removed from the device. This arrangement may provide for a convenient and easy way for a user to prepare the device for use as well as open a dose chamber for dose delivery.

In some embodiments, the cover includes a cap that covers the outlet of the mouthpiece. The cap may cover only the outlet end of the mouthpiece, e.g., to prevent contamination of a portion of the mouthpiece that a user puts in his mouth during use. The cap may be connected to the seal by a clip, such as a strip of sheet material, such that removal of the cap from the mouthpiece removes the seal from its position in which fluid communication between the dose chamber and the air path is resisted.

In another embodiment, the cover includes a layer of barrier material that completely surrounds the body and the dose chamber. For example, the cover may include a sheet of foil material that is wrapped around the body and sealed to itself to completely enclose the body and dose chamber. In another embodiment, the cover includes a pair of barrier layers, with a first layer of the pair of barrier layers forming a blister in which the body and the dose chamber are positionable, and a second layer of the pair of barrier layers is sealed to the first layer to enclose the blister. Separation of the cover from the inhaler may cause the seal to open fluid communication between the flow path and the dose chamber, e.g., a portion of the cover may be attached to the seal, which is removed with the cover. In one embodiment, a portion of the barrier layer near the mouthpiece outlet may be attached to a tab that extends to the seal. In an embodiment in which a handle of the body extends opposite the mouthpiece, a user may grip the handle and a portion of the barrier layer near the mouthpiece and pull the two apart to withdraw the body from the cover as well as remove the seal from its sealing position.

In some embodiments, the seal may include a wall that is slidably engaged with the body and is guided in movement relative to the body when moved from a closed or sealing position to an open position upon removal of the cover. For example, the seal may include a U-shaped channel portion that engages with a rail section of the body that guides movement of the channel portion along the rail during movement of the seal from the sealing position to the open position.

The dose chamber may take a variety of different forms, and in one embodiment has a spoon shape and is arranged to engage the body at a "handle" portion of the spoon shape. Dose may be located in the "spoon" portion, which may be arranged to facilitate fluidization and entrainment of dose in air flowing in the dose chamber. As noted above, the dose chamber may include two or more spaces, e.g., two separate spaces in which dose is located and is deliverable to the flow path. Flow into and out of the dose chamber may be arranged in different ways, and may depend on the amount and/or characteristics of dose to be delivered. In some embodiments, an obstacle such as a curved surface may deflect air flow in the flow path into the dose chamber. For example, inhalation of a user may cause flow in the air path, and a portion of that flow may be deflected into the dose chamber, causing the deflected air to entrain dose. The dose entrained air may then exit the dose chamber into the flow path and pass to the mouthpiece outlet. Dose entering the flow path may do so in different ways, e.g., the dose chamber and the body may be arranged such that dose-entrained air flowing from the dose chamber to the flow path enters the flow path in a direction perpendicular to flow in the flow path. Alternately, or additionally, the dose-entrained air flowing from the dose chamber to the flow path may enter the flow path at a restriction in the flow path. One or more inlets or outlets to the dose chamber may be defined by the dose chamber itself, by the body and the dose chamber and/or by the body itself.

The seal may be configured in different ways, e.g., as a sheet of barrier material that is sandwiched between the dose chamber and the body so as to seal the dose chamber closed. In other arrangements, the seal may engage the body only to resist fluid communication with the dose chamber, or may engage the dose chamber only. Also, the seal may be configured to extend in a desired way such that removal of the cover moves the seal to an open position or otherwise permits fluid communication with the dose chamber. For example, the seal may include a portion that extends from the outlet of the mouthpiece and inside the mouthpiece along the flow path to a position near the dose chamber. This arrangement may help prevent a user from attempting to inhale a dose without first opening the dose chamber, e.g., because a portion of the seal may be positioned at the mouthpiece outlet, providing a reminder to open fluid communication with the dose chamber. In another arrangement, the seal may include a portion that extends along an outer surface of the mouthpiece to a position near the dose chamber. This may allow a user to grasp the seal near the mouthpiece and pull the seal to release dose for delivery.

Other aspects, features and advantages will be apparent from the description of the following embodiments and from the claims.

BRIEF DESCRIPTION OF THE DRAWINGS

These and other features and advantages will be better understood by reading the following detailed description, taken together with the drawings wherein.

DETAILED DESCRIPTION

In at least some embodiments, delivery devices described herein include one or more dose chambers for storing and delivering a dose of a substance, such as a powdered medicament, including blended formulations, excipient formulations, neat formulations or combinations thereof, or flavorant, or vaccine, to a subject. The dose chamber may be placed in fluid communication with an air pathway to ready the dose for delivery to the subject. Air may be drawn or pushed through the air pathway so that at least a portion of the air enters the dose chamber to entrain the dose. Air may then exit the dose chamber, laden with powder from the dose chamber, and move toward an outlet of the delivery device to a subject. Though embodiments are described with reference to embodiments that include a mouthpiece, it is to be understood that such embodiments may be used to deliver dose in nasal or other pulmonary delivery techniques. Thus, the embodiments are not limited to use with a user's mouth.

According to some aspects, a dose delivery device may include an opening mechanism attached to a cover that at least partially surrounds a portion of a mouthpiece. For example, a removable mouthpiece cap may integrate a sealing mechanism to close fluid communication between the dose chamber and the mouthpiece. Thus, in one aspect of the invention, a dose delivery device may be arranged so that a mouthpiece and the cap are movable relative to each other to form an opening in the dose chamber for delivery of the dose. Such an arrangement may make use of the device relatively simple, e.g., a user may both open the dose chamber and expose a mouthpiece under the cover in a single operation.

Figure 1:
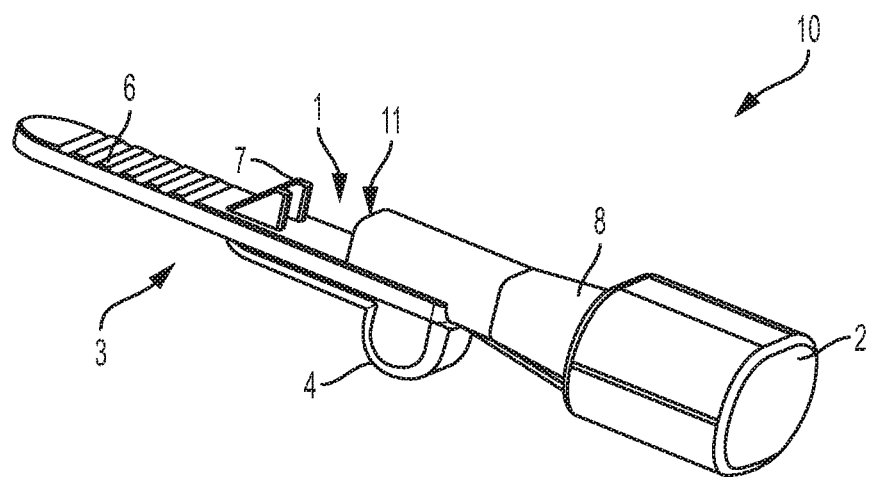
FIG. 1 shows a perspective view of an illustrative dose delivery device.
Figure 6:
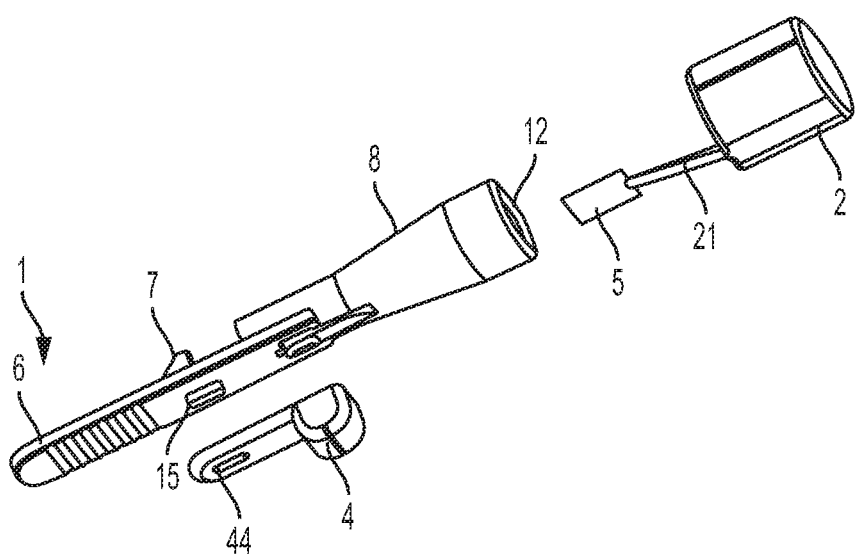
FIG. 6 shows an exploded view of the FIG. 1 embodiment.

FIG. 1 shows one illustrative embodiment of a dose delivery device 10 in a stored state. That is, in the configuration shown in FIG. 1, the delivery device 10 is not ready for use in delivering a dose because a cover 2 is positioned to cover at least a portion of a mouthpiece 8. Removal of the cover 2 from the mouthpiece 8, described in more detail below, exposes an outlet opening of the mouthpiece 8 and opens fluid communication between a flow path of the mouthpiece 8 and a dose chamber 4 that contains a dose (not shown). In this embodiment, the mouthpiece 8 is part of a body 1 that defines a handle 6 which may be gripped by a user, and a thumb guard 7 which may help prevent a user from positioning a thumb or finger at an inlet 11.

Figure 2:
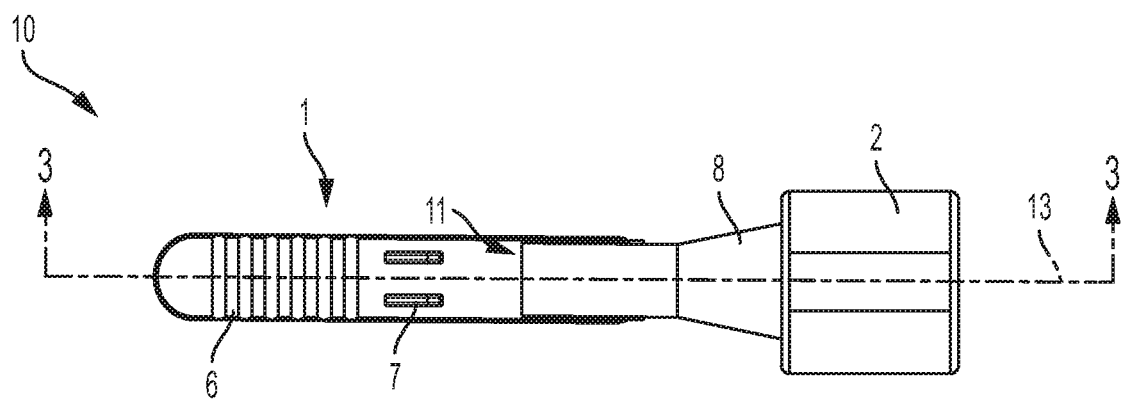
FIG. 2 shows a top view of the FIG. 1 embodiment.
Figure 3:
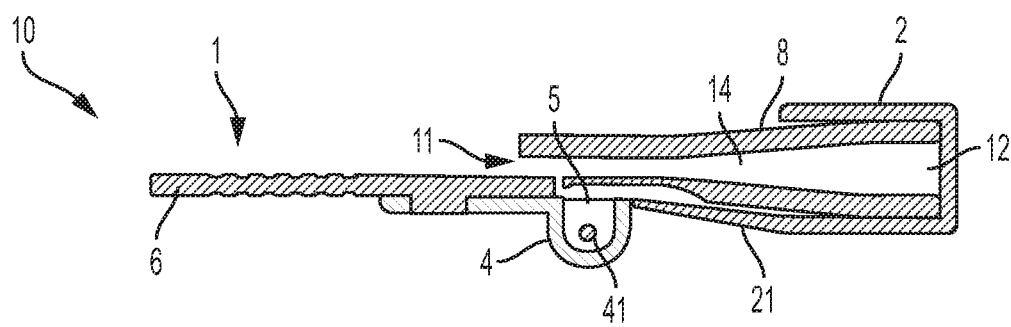
FIG. 3 shows a cross sectional side view of the FIG. 1 embodiment with a cover attached and the dose chamber sealed.

FIG. 2 shows a top view of the FIG. 1 embodiment, and FIG. 3 shows a cross-sectional side view along the line 3-3 in FIG. 2. As can be seen in FIG. 3, the body 1 defines a flow path 14 that extends from the inlet 11 to an outlet 12, which is covered by the cover 2. In this embodiment, the flow path 14 extends along an axis 13 (see FIG. 2), but other arrangements are possible, such as a flow path 14 that includes one or more curved or other non-linear sections. A seal 5 is arranged to resist fluid communication between the dose chamber 4 where a dose 41 is located and the flow path 14. This may help keep the dose 41 fresh, sterile, and/or otherwise suitable for delivery to a user. In this embodiment, the seal 5 includes a layer of barrier material, such as a foil/polymer laminate, but other arrangements are possible, such as a sheet of thicker plastic or other material, a sliding door, a valve, etc.

Figure 4:
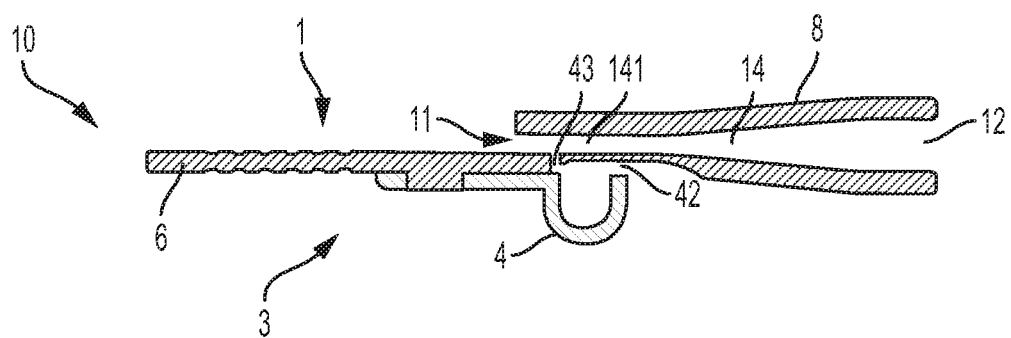
FIG. 4 shows a cross sectional side view of the FIG. 1 embodiment with the cover removed and the dose chamber is opened.
Figure 7:
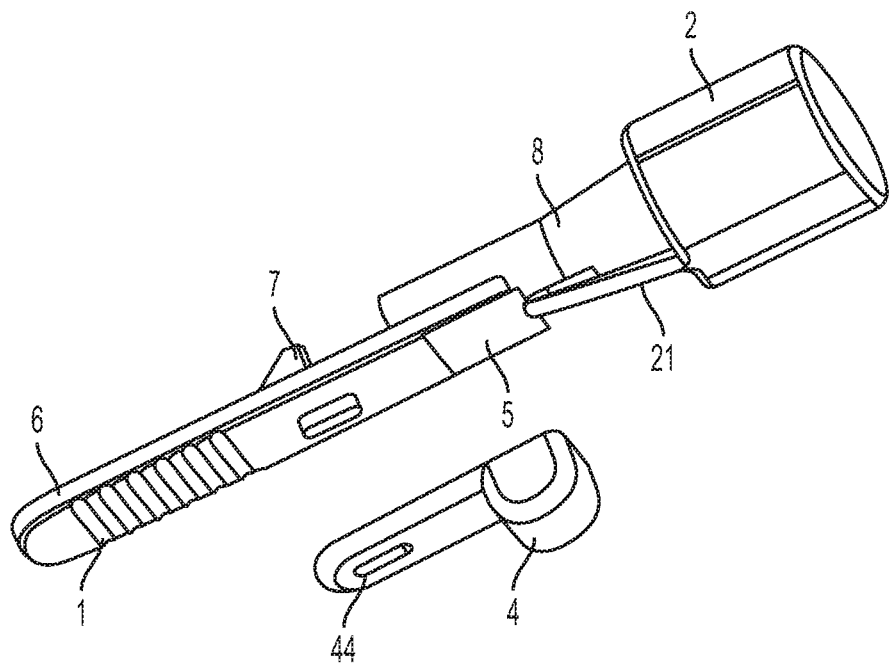
FIG. 7 shows a partially exploded view of the FIG. 1 embodiment with the dose chamber separated to show the sealing mechanism during assembly.
Figure 5:
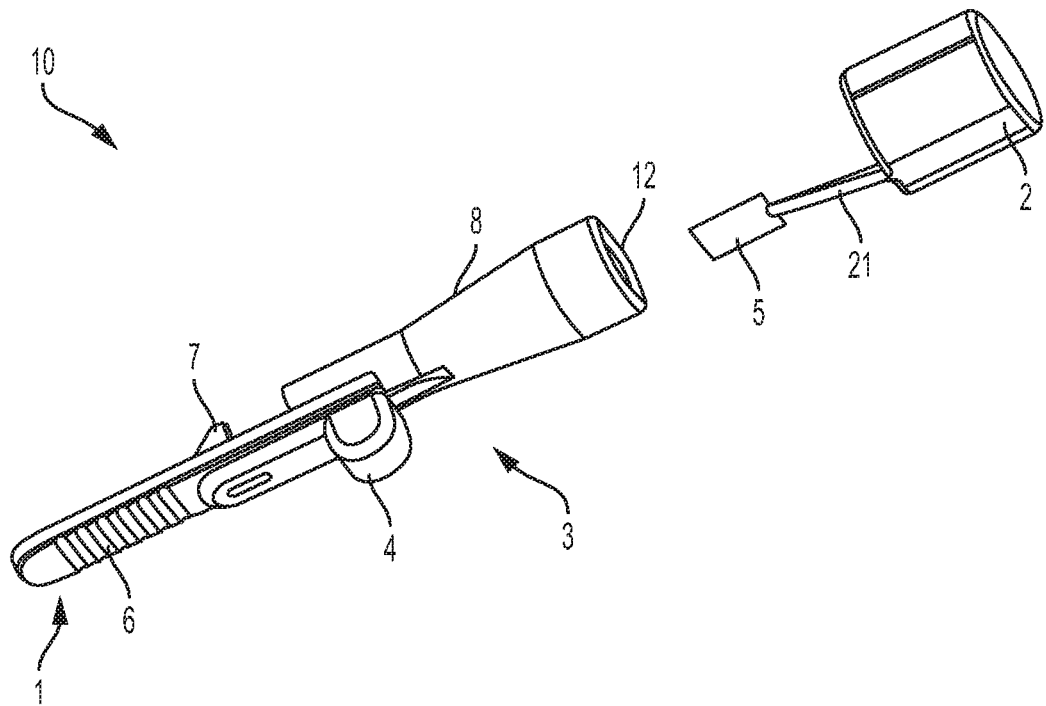
FIG. 5 shows a bottom perspective view of FIG. 1 embodiment with the cover and seal removed.

In this embodiment, the cover 2 is attached to a seal 5 via a clip or tab 21 such that removal of the cover 2 from the mouthpiece 8 pulls the seal 5 to the right from its closed or sealing position shown in FIG. 3. Though not necessary, the cover 2 engages the mouthpiece 8 such that movement of the cover 2 during its removal is guided in a linear direction that causes effective removal of the seal 5 from its closed position. FIG. 4 shows the cross-sectional view of FIG. 3 and FIG. 5 shows a front, bottom perspective view of the device 10 with the cover 2 and seal 5 removed. (The assembly of the body 1 and dose chamber 4 having the cover 2 removed is referred to as an inhaler 3 for ease of reference.) Removal of the seal 5 exposes an opening of the dose chamber 4 such that fluid communication between the dose chamber 4 and the flow path 14 is open. Although in this embodiment and others, the seal 5 is removed from the inhaler 3, the seal 5 need not necessarily be removed, e.g., the seal 5 may simply be moved, pierced, deformed or otherwise altered in position or state to permit fluid communication with the dose chamber 4. For example, in the FIG. 1 embodiment, the seal 5 may be slid to open the dose chamber 4, but then stop in its movement such that the tab 21 disconnects from the seal 5.

In this embodiment, movement of air along the flow path 14 from the inlet 11 to the outlet 12 causes air to be drawn into the dose chamber 4 via an inlet opening 42. In this embodiment, the inlet opening 42 is defined by the body 1 and the dose chamber 4, but the inlet opening could be defined by the body 1 alone or by the dose chamber 4 alone. Air flow into the dose chamber 4 causes dose 41 to be entrained in the air, and dose-entrained air exits the dose chamber to the flow path 14 via an outlet opening 43. In this embodiment, the body 1 defines the outlet opening 43, but the outlet opening could be defined by the dose chamber 4, or by the dose chamber 4 and the body 1. Also, two or more inlet or outlet openings 42, 43 may be provided in some embodiments. Dose-entrained air exiting the dose chamber 4 at the outlet opening 43 enters the flow path 14 at a restriction 141 and enters in a direction perpendicular to a direction of flow in the flow path 14. This may aid in the dispersion of dose in the flow path, e.g., by helping to further break down small particles of dose if needed. However, other configurations are possible, such as introducing dose-entrained air parallel to flow in the flow path or at other angles. In another embodiment, the flow path 14 may not include inlet 11 and may be defined by flow through inlet opening 42, outlet opening 43 and outlet 12.

Another aspect of the invention incorporated into this embodiment is that the handle 6 is arranged so as to provide ergonomic advantages, e.g., a user's grasping the handle 6 in a natural way, similar to the way a lollipop is held, can orient the inhaler 3 for easy use. That is, natural holding of the handle 6 may position the mouthpiece 8 properly for communication with a user's mouth. In addition, the inhaler 3 may be held such that dose 41 in the dose chamber 4 does not fall out of the chamber 4 after the seal 5 is removed. For example, in this embodiment, the inlet opening 42 and the mouthpiece outlet 12 face away from the handle 6, and thus if the inhaler 3 is held by the handle 6, the inlet opening 42 and outlet 12 will face generally upwardly, helping to prevent dose 41 from falling out of the inhaler 3.

FIG. 6 shows an exploded view of the delivery device 10 and helps to illustrate how the dose chamber 4 is engaged with the body 1 in this embodiment. That is, the dose chamber 4 includes a slot or opening 44 that receives a pin or protrusion 15 on the body 1, and engagement of the slot 44 and pin 15 positions the dose chamber 4 appropriately both in directions along a length of the body 1 and in a side-to-side direction. This positioning can be important since the dose chamber 4 and the body 1 cooperate to define inlet and outlet openings 42, 43 for the dose chamber 4, and because the dose chamber 4 should properly engage with the seal 5 and/or body 1, e.g., to help prevent dose 41 from escaping in undesired ways. For example, during assembly of the device 10, the cover 2 and the attached seal 5 may be engaged with the body 1 before the dose chamber 4 is attached to the body 1, as shown in FIG. 7. This positions the seal 5 appropriately such that when the slot 44 receives the pin 15, the seal 5 is positioned over the opening of the dose chamber 4 so as to seal the dose chamber 4 closed when the seal 5 is sandwiched between the dose chamber 4 and the body 1. That is, the seal 5 may be squeezed between the dose chamber 4 and the body 1 so that the dose chamber 4 is suitably closed without adhering the seal 5 to the dose chamber 4, although such positive connection between the two is possible. The slot 44 and pin 15 may be engaged with each other by an interference fit to properly engage the dose chamber 4 and body 1 and to trap the seal 5 in place. Engagement of the dose chamber 4 with the body 1 may bias the dose chamber 4 toward the body 1 such that when the seal 5 is removed, the dose chamber 4 may move toward the body 1 to close any gaps between the dose chamber 4 and the body 1 (other than the gap at the inlet opening 42). For example, a portion of the dose chamber 4 may act as a sort of leaf spring that biases the dose chamber 4 into engagement with the body 1. Alternately, the dose chamber 4 and/or body 1 may include a groove or recess in which the seal 5 is received, allowing the dose chamber 4 to abut the body 1 in areas around the dose chamber opening both before and after removal of the seal 5. Also, although in this embodiment the body 1 includes a pin 15 that engages with an oval slot 44 of the dose chamber, the cross sectional shape of the pin or other protrusion 15 and shape of the slot or other opening 44 is not limited to an oval shape and may be many shapes or multiple instances of shape. Furthermore, the use of a protrusion/opening engagement is not necessary, and the dose chamber 4 and body may be attached by other means such as the use of adhesives, heat staking, ultrasonic or RF welding, one or more fasteners, or other means of joining materials.

Figure 8:
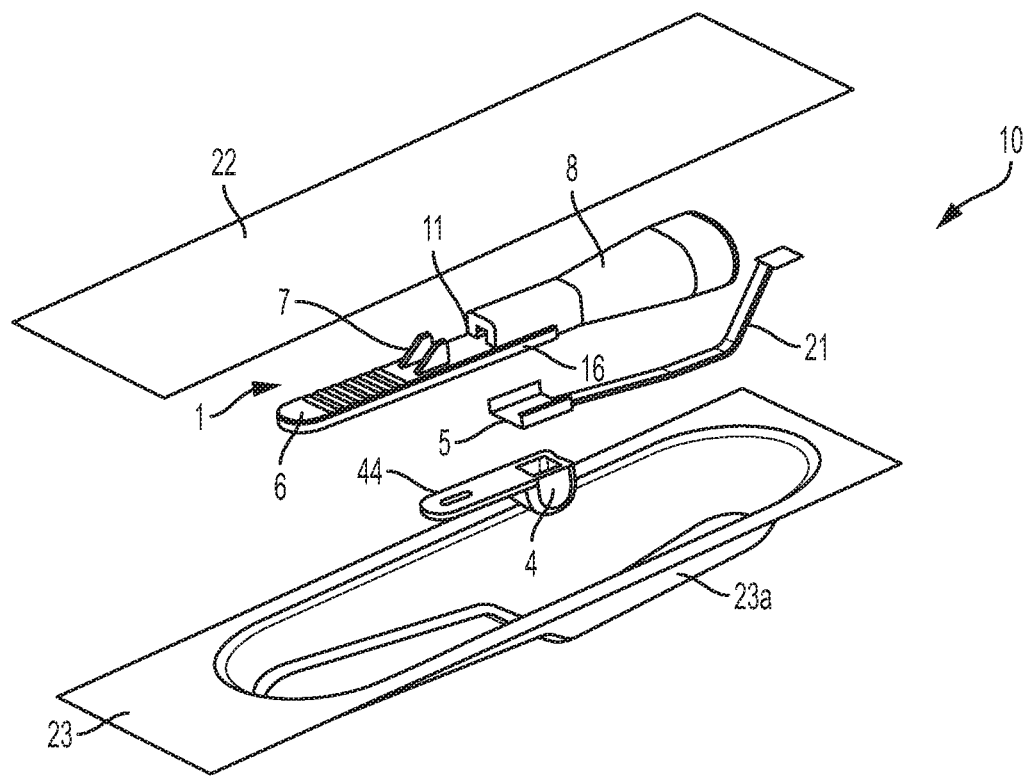
FIG. 8 shows an exploded view of yet another illustrative embodiment in which the sealing mechanism is part of a cover that completely encapsulates the device.
Figure 9:
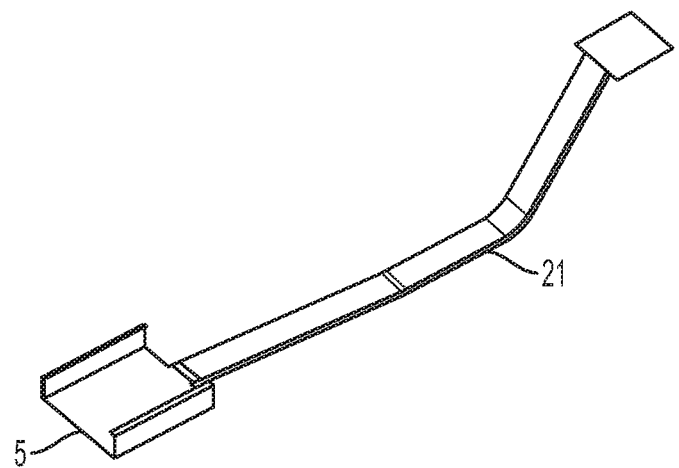
FIG. 9 shows a perspective view of the FIG. 8 sealing mechanism.
Figure 10:
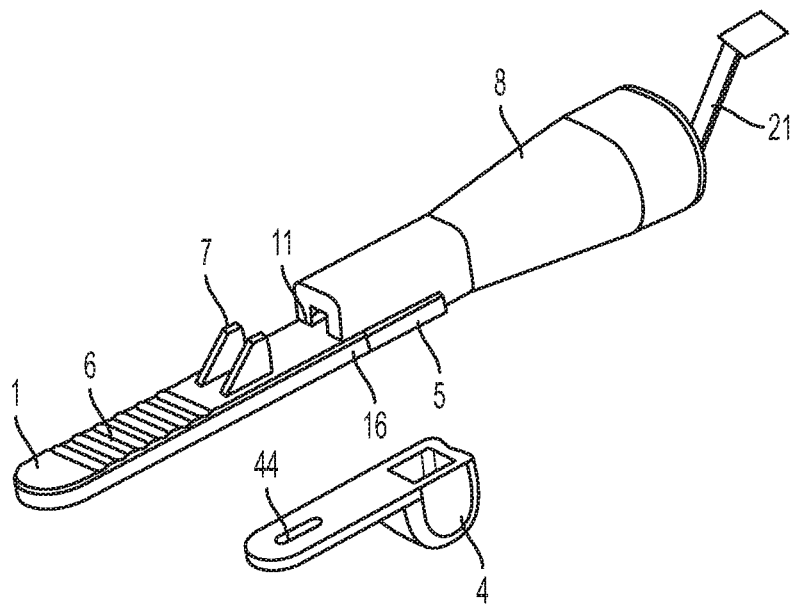
FIG. 10 shows a partially exploded view of the FIG. 9 sealing mechanism attached to the mouthpiece and the dose chamber positioned for filling and attachment to the inhaler.

FIG. 8 shows an exploded view of another illustrative embodiment of a dose delivery device 10. In this arrangement, the body 1 and dose chamber 4 are arranged in the same way as in the FIG. 1 embodiment. However, in this arrangement, the seal 5 includes a channel element that has a U-shaped cross section, which is shown in close up in FIG. 9. As shown in FIG. 10, the channel element 5 is arranged to receive a rail portion 16 of the body 1 such that movement of the channel element 5 is guided by the rail portion 16. That is, the channel element 5 is guided in motion relative to the body 1 so that the channel element 5 moves along a length of the body 1 (or in a direction along the axis 13 of the flow path 14) until the channel element 5 disengages from the body 1 and the dose chamber 4 is opened for fluid communication with the flow path 14. In this way, a user can be assured of properly removing the seal 5 in a way that will reliably and accurately open the dose chamber 4 for fluid communication. It should be understood that the rail 16 could be provided on the dose chamber 4, or provided by both the body 1 and the dose chamber 4.

Figure 11:
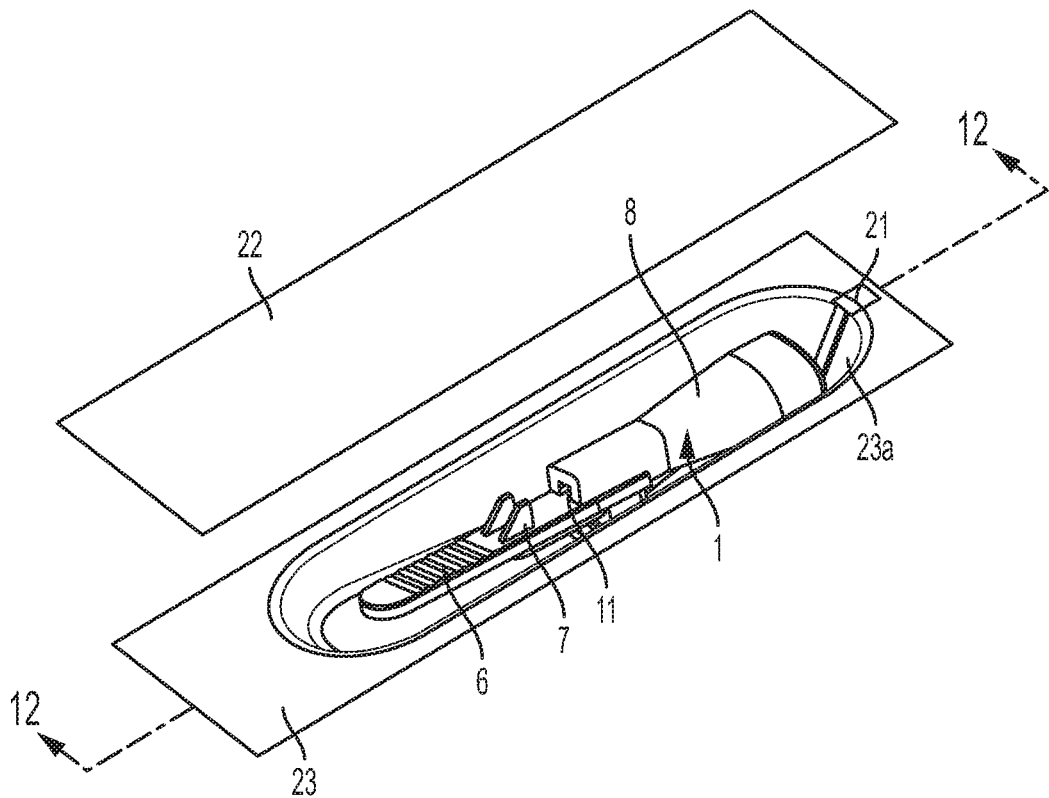
FIG. 11 shows a perspective view of the FIG. 10 inhaler assembly loaded into an external blister package.
Figure 12:
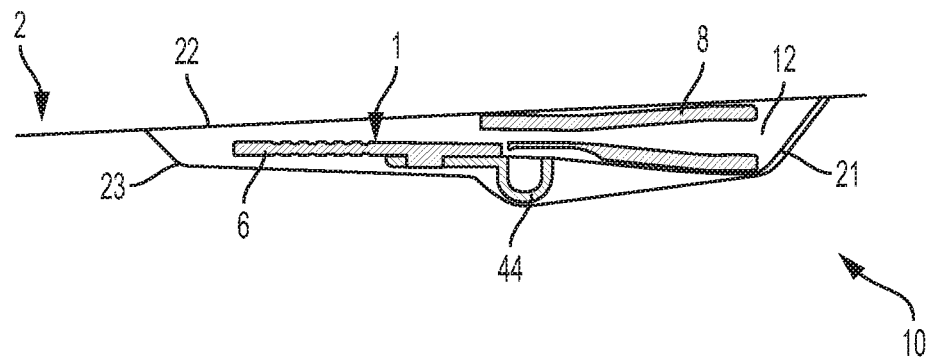
FIG. 12 shows a cross sectional side view of the FIG. 11 inhaler assembly.

Another difference between this embodiment and that of FIG. 1 is that the cover 2 in this FIG. 10 embodiment completely surrounds the body 1 and dose chamber 4. Although the cover 2 could be arranged in other ways, the cover 2 includes a first portion 22 in the form of a sheet of barrier material that is joined to a second portion 23 which also includes a sheet of barrier material. However, the second portion 23 is formed to include a blister 23a, e.g., a cavity, arranged to receive the body 1 and the dose chamber 4 such that the first portion 22 can be positioned over the second portion 23 and the two portions 22, 23 sealed together to enclose the inhaler 3. As illustrated in FIG. 11 a distal portion of the clip or tab 21 may be positioned between the first and second portions 22, 23 in an area near the outlet 12 of the mouthpiece 8 and extend along a length of the mouthpiece 8 to the dose chamber 4. Thus, the tab 21 may be joined to the first and second portions 22, 23 when the two portions 22, 23 are joined together. FIG. 12 shows a cross sectional view of the device 10 in an assembled condition with the inhaler 3 fully enclosed by the cover 2 and the tab 21 trapped between the first and second portions 22, 23 near the outlet 12 of the mouthpiece.

Figure 13:
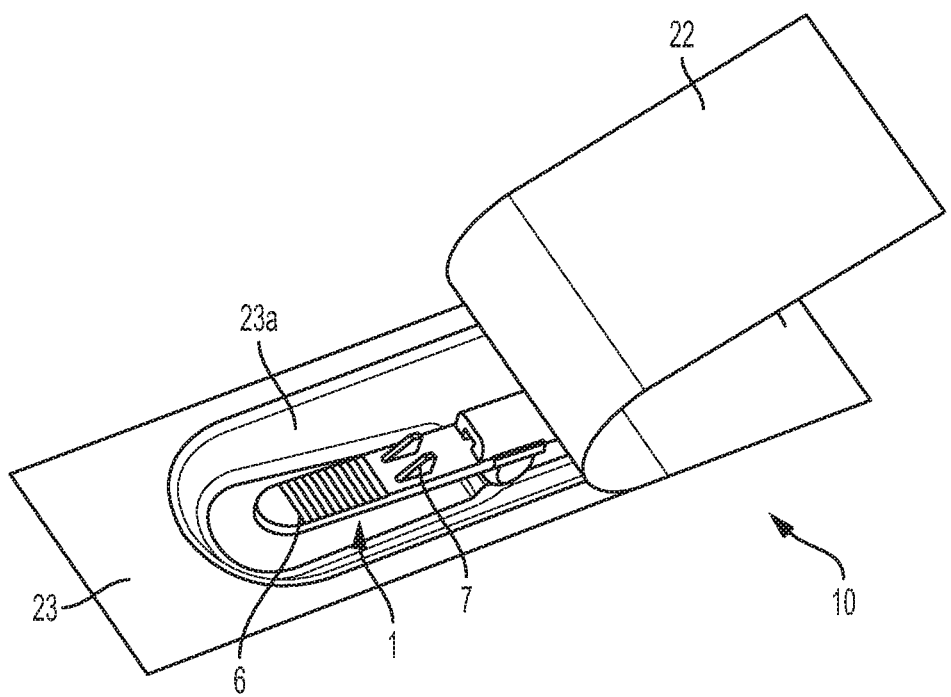
FIG. 13 shows the FIG. 12 embodiment with the external packaging opened to present the inhaler handle in an ergonomic manner.
Figure 14:
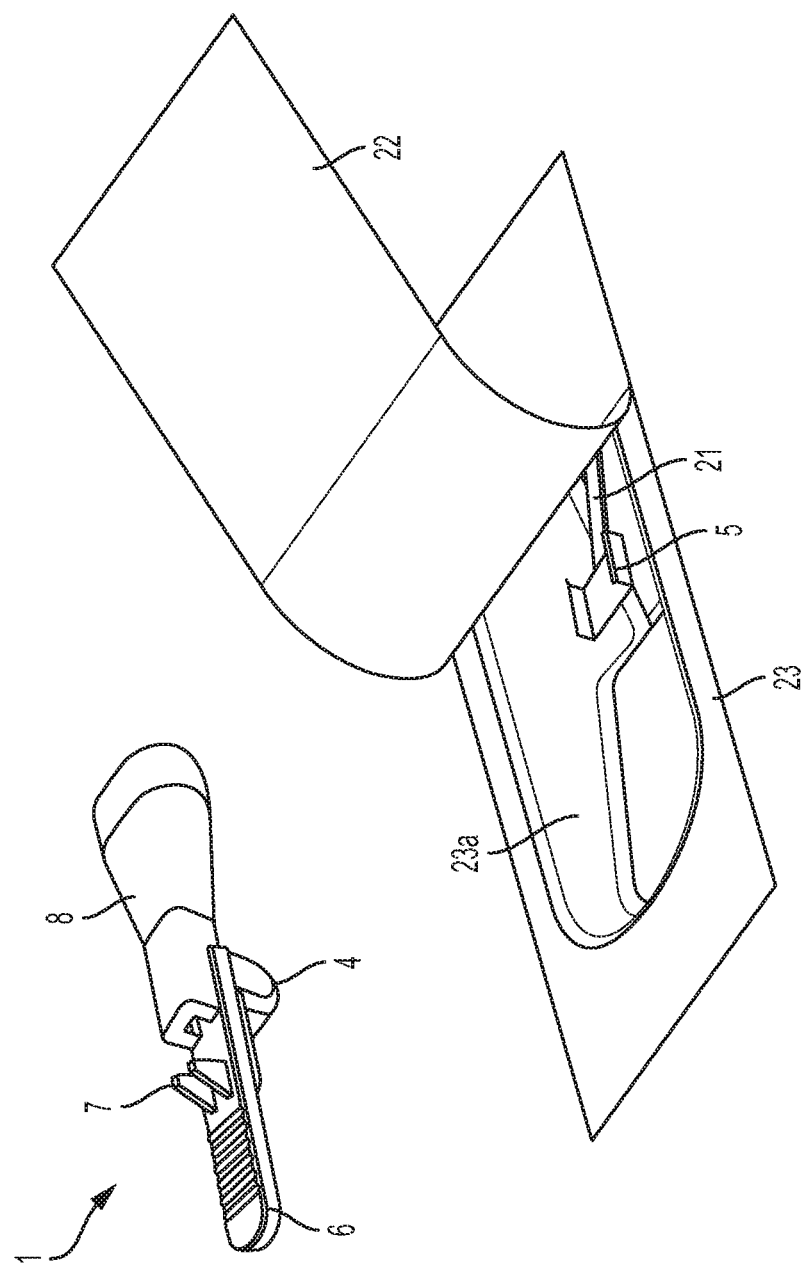
FIG. 14 shows an exploded view of the inhaler assembly withdrawn from the external packaging with the sealing mechanism remaining attached to the packaging.

To remove the inhaler 3 from the blister 23a, the first portion 22 of the cover 2 may be peeled back from the second portion 23 to a position shown in FIG. 13. Then, a user may grasp the handle 6 in one hand while grasping the cover 2 in an area where the tab 21 is joined to the first and second portions 22, 23 and pull the handle 6 so as to remove the inhaler 3 from the blister 23a. This causes the seal 5 to slide along the rail 16 of the body 1 until the seal 5 disconnects from the body 1 and the inhaler 3 can be removed as shown in FIG. 14. In another embodiment, a portion of the handle 6 may include a knife edge, pointed section, or other energy director that can be used to pierce the cover 2 from the inside and allow the handle 6 to be extended outside of the cover 2. Thereafter, a user may grasp the exposed handle 6 and pull the body 1 from the cover 2. For example, a user may grasp the device 10 so that the mouthpiece 8 portion is held in one hand and a portion of the cover 2 near the handle 6 is held in the other hand. The user may then pull the cover 2 portion toward the mouthpiece 8, causing a part of the handle 6 to pierce and extend through the cover 2. The user may then grasp the exposed handle 6 and pull the body 1 from the cover 2.

Figure 15:
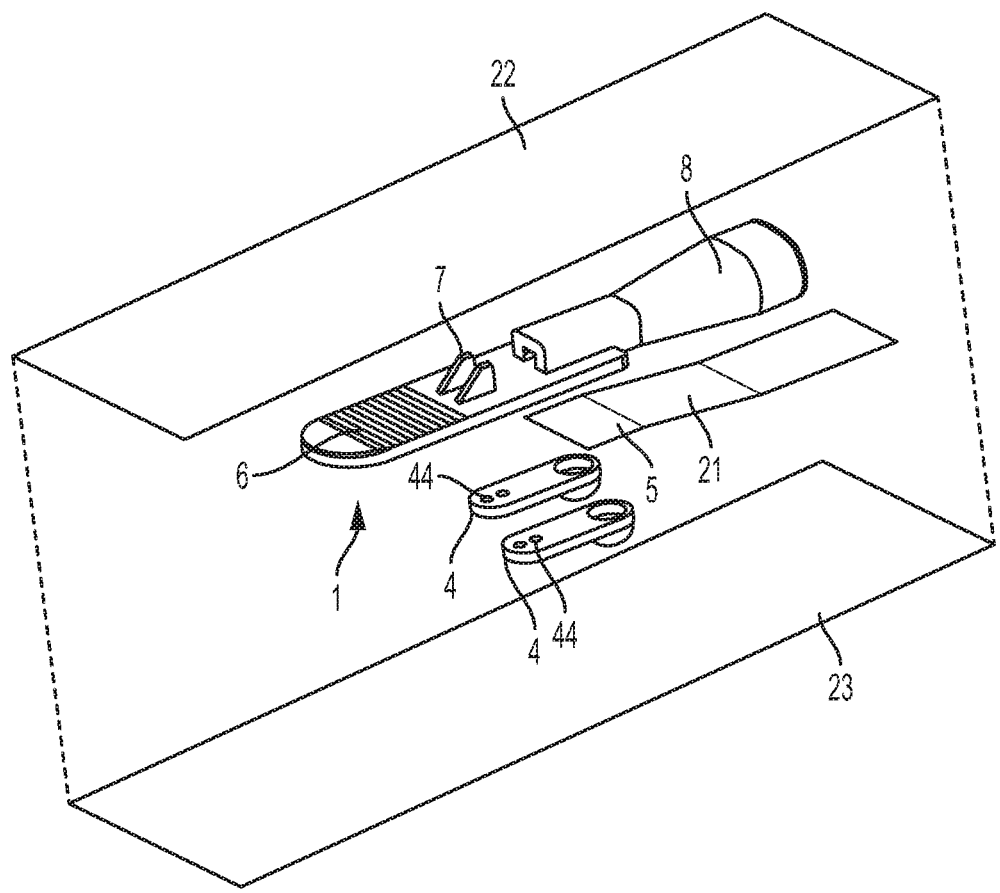
FIG. 15 shows an upper side exploded view of an alternative embodiment wherein the sealing mechanism is a thin strip of material and the device includes two dose chambers.
Figure 16:
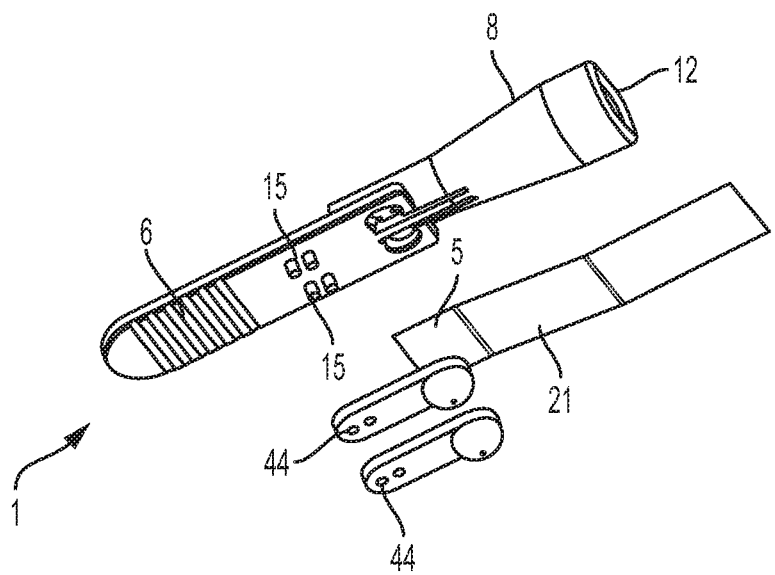
FIG. 16 shows an exploded view of the lower side of the device and sealing mechanism of FIG. 15.

FIG. 15 shows an exploded view of another embodiment that is similar to the one shown in FIG. 8. However, this embodiment differs in that the device 10 includes two dose chambers 4 rather than one, and the second portion 23 of the cover 2 does not include a blister 23a. FIG. 16 shows a bottom perspective view of the body 1 and dose chambers 4 in the FIG. 15 embodiment. As can be seen, the two dose chambers 4 are engaged with the body 1, except that in this embodiment the dose chambers include a pair of openings 44 that each receive a cylindrical pin 15 rather than having a single oval opening that receives an oval protrusion. Similar to the FIG. 1 embodiment, a seal 5 in the form of a layer of barrier material is trapped between the dose chambers 4 and the body 1 to close the dose chambers 4. In this arrangement, once the seal 5 is removed, the dose in both chambers 4 may be delivered simultaneously to a user. However, it is possible to arrange the seal 5 in two sections that may be separately removed so that the dose in the two chambers 4 may be delivered sequentially.

Figure 17:
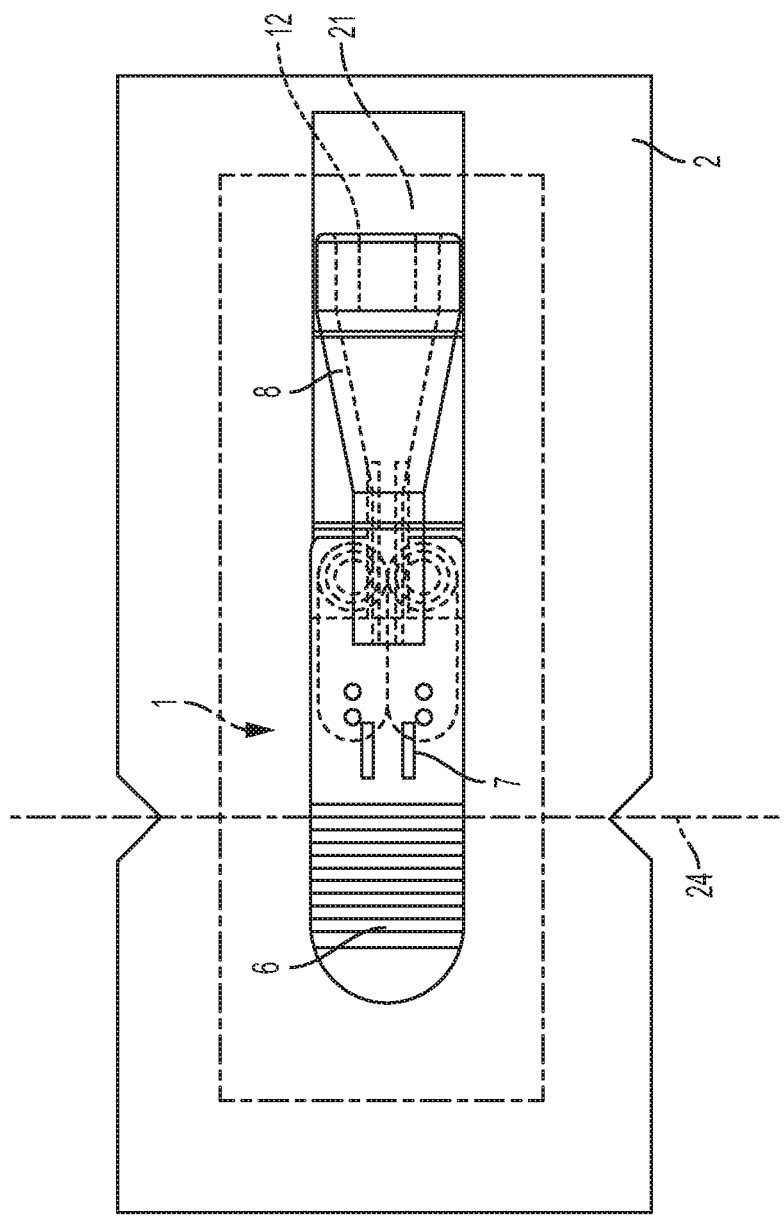
FIG. 17 shows a top view of the FIG. 15 embodiment enclosed in an external package.

As can be seen in FIG. 17, when the inhaler 3 is enclosed in the cover 2, the tab 21 may be joined to the first and second portions 22, 23 in an area near the outlet 12 of the mouthpiece. The cover 2 may also be provided with a line of weakness 24 which may include one or more notches cut into the cover 2, a scoring of the first or second portions 22, 23 along the line 24, a perforation, or other arrangement that tends to cause the cover 2 to separate along the line 24 when a user pulls the portion of the cover 2 at the handle 6 from the portion of the cover 2 at the tab 21 apart. That is, a user may grasp the handle 6 through the cover 2 as well as the tab 21 and pull the cover so as to pull the body 1 from the portion of the cover 2 on the right in FIG. 17. This causes the seal 5 to be removed from the inhaler 3. Thereafter, the portion of the cover on the left of FIG. 17 may be removed from the handle 6, if desired. Alternately, a user may first tear the cover 2 at the line of weakness 24 and remove the portion of the cover 2 from the handle 6. Thereafter, the user may grasp the now exposed handle 6 and pull the inhaler 3 from the remaining portion of the cover 2 positioned over the mouthpiece 8.

Figure 18:
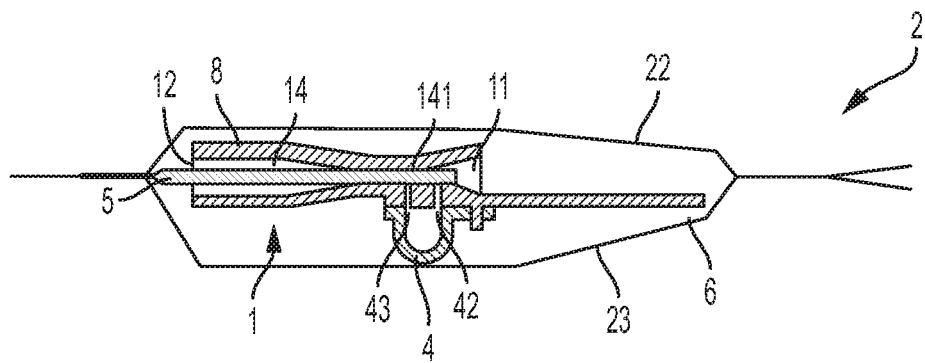
FIG. 18 shows a cross sectional side view of an alternative embodiment wherein the sealing mechanism closes fluid communication between the air path and dose chamber.
Figure 19:
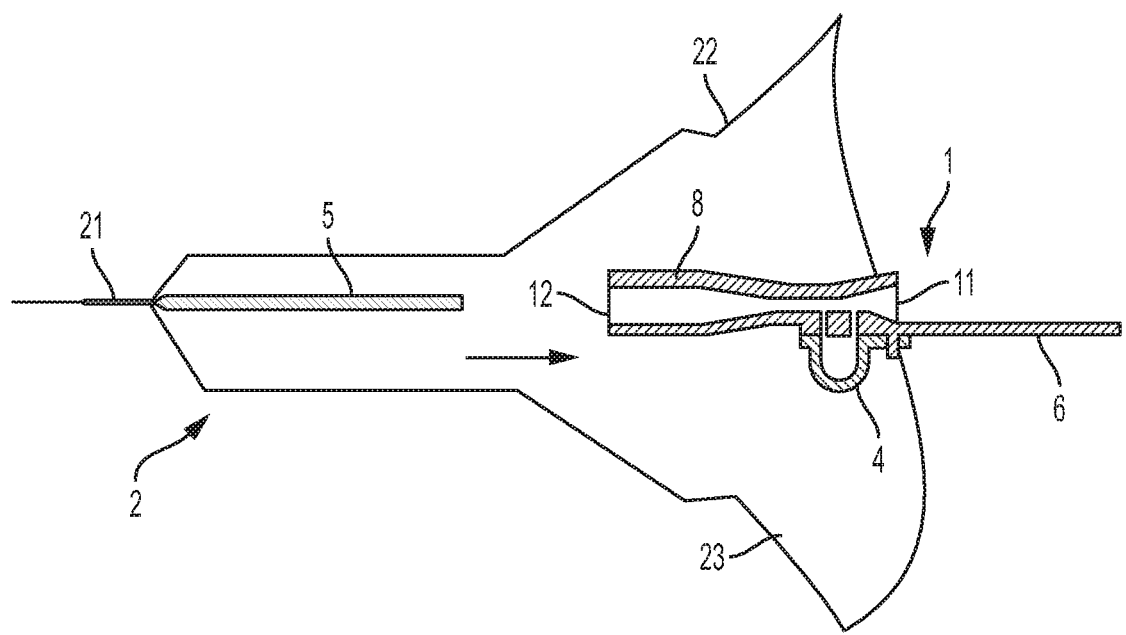
FIG. 19 shows a cross sectional side view of the FIG. 18 embodiment wherein the package is open, the device removed and the dose chamber is ready for inhalation.

FIGS. 18 and 19 show a cross sectional side view of another embodiment that is similar to the FIG. 8 embodiment. However, in the FIGS. 18 and 19 embodiment, the seal 5 extends through the outlet 12 of the mouthpiece 8 and down the flow path 14 to a position over the dose chamber 4 where the seal 5 closes inlet and outlet openings 42, 43. The seal 5 may be adhered to the body 1 to close the openings 42, 43, or may fit in the flow path 14 with an interference fit to block the openings 42, 43, e.g., the size and shape of the seal 5 may closely match the size and shape of the restriction 141. To use the device 10, the first and second portions 22, 23 may be separated by peeling the portions 22, 23 apart at the handle 6 end of the body 1. Thereafter, a user may grasp the handle 6 and pull the seal 5 from the flow path 14 to open the dose chamber 4 as shown in FIG. 19.

Figure 20A:
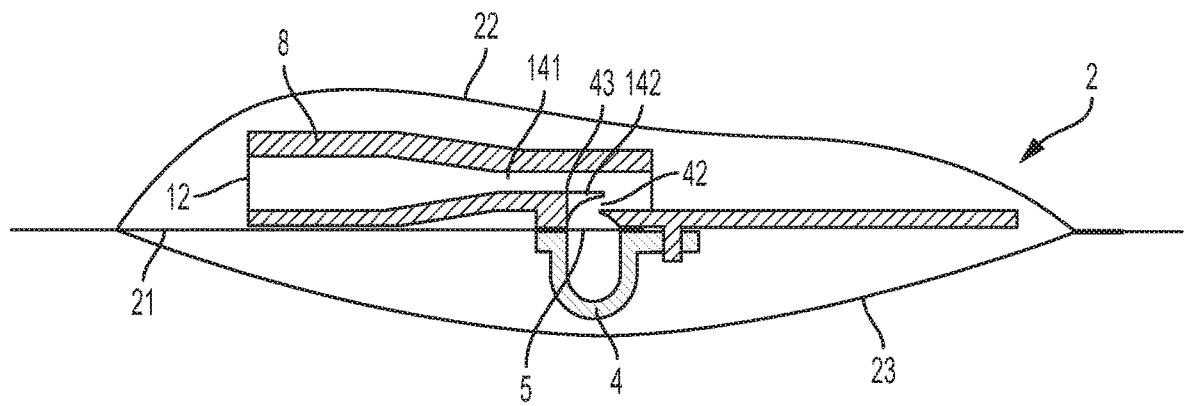
FIG. 20A shows a cross sectional side view of an alternative embodiment with crossing air flow in the dose chamber.
Figure 20B:
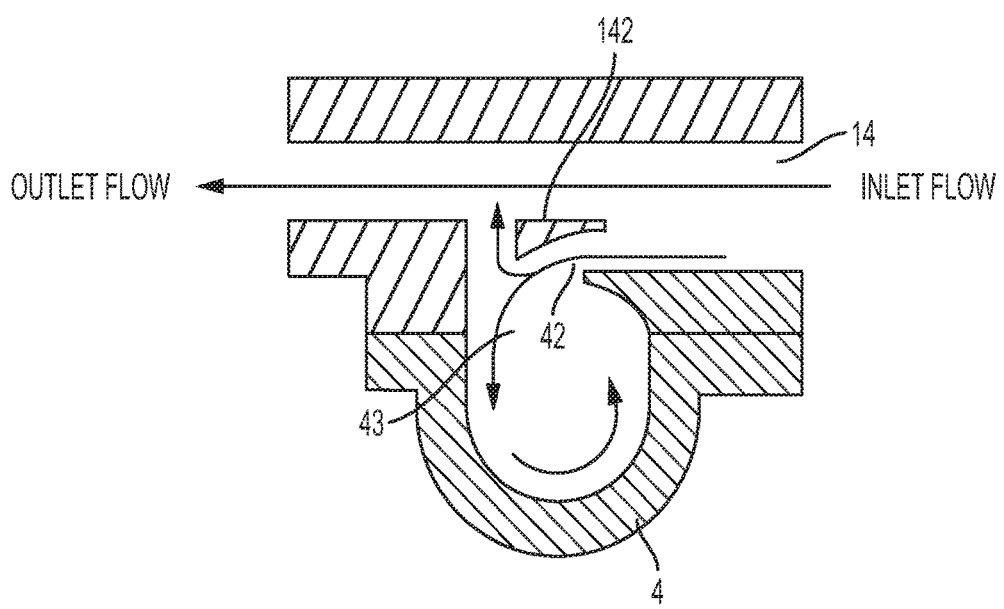
FIG. 20B shows a cross sectional side schematic of the air flow in the FIG. 20A embodiment.

As noted above, the body 1 and/or dose chamber 4 may be arranged to provide different flow arrangements in the dose chamber 4. For example, FIG. 20A shows an arrangement in which the inlet opening 42 of the dose chamber 4 is arranged in the flow path 14. An obstacle 142 is shaped and configured to divert air flow in the flow path 14 into the dose chamber 4, and an outlet opening 43 is arranged downstream of the inlet opening 42 to introduce dose-entrained air from the dose chamber 4 into the flow path 14 in a direction perpendicular to flow in the flow path 14. FIG. 20B shows the flow in the dose chamber 4, i.e., flow into the chamber 4 is deflected downward into the chamber 4 and circulates back toward the inlet opening 42. Also, in this configuration, some of the flow entering the inlet opening 42 may pass directly to the outlet opening 43.

Figure 21A:
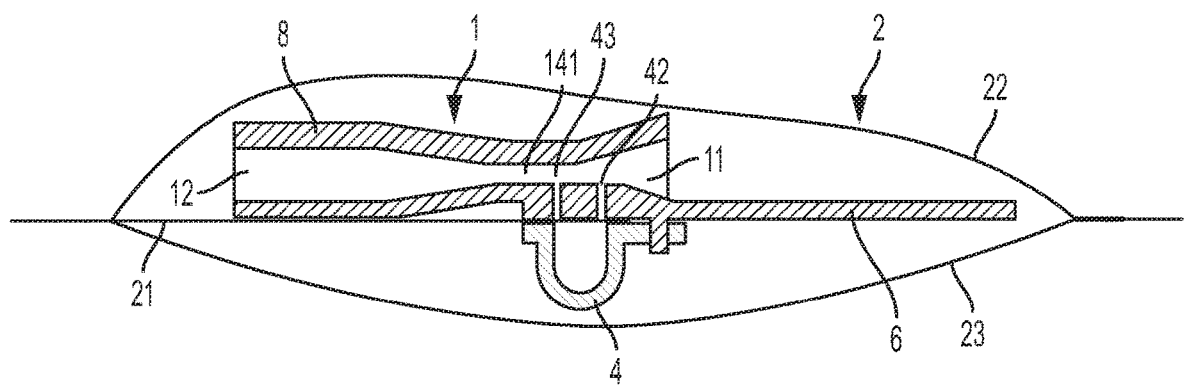
FIG. 21A shows a cross sectional side view of an alternative embodiment with air flow entering the dose chamber from the flow path and following a U shape path in the dose chamber.
Figure 21B:
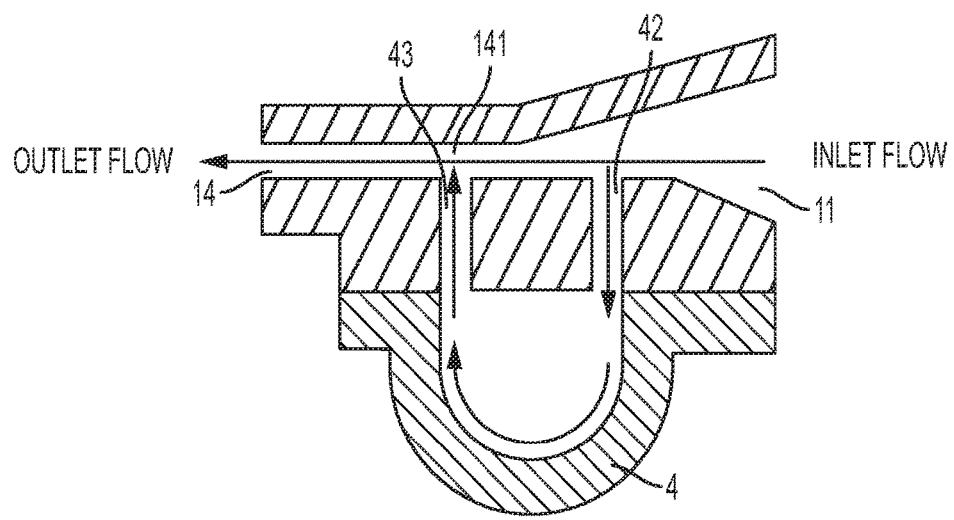
FIG. 21B shows a cross sectional side schematic of the air flow in the FIG. 21A embodiment.

FIG. 21A shows another arrangement in which the inlet and outlet openings 42, 43 are arranged in the flow path 14 and are oriented generally perpendicularly to flow in the restriction 141. FIG. 21B shows the flow in the dose chamber 4. Flow enters the dose chamber 4 via the inlet opening 42 in a downward direction, and is deflected back upwardly toward the outlet opening 43. In this embodiment, the dose-entrained air exits the dose chamber 4 and enters the flow path 14 in a direction perpendicular to flow in the flow path 14 and at a restriction 141.

Figure 21C:
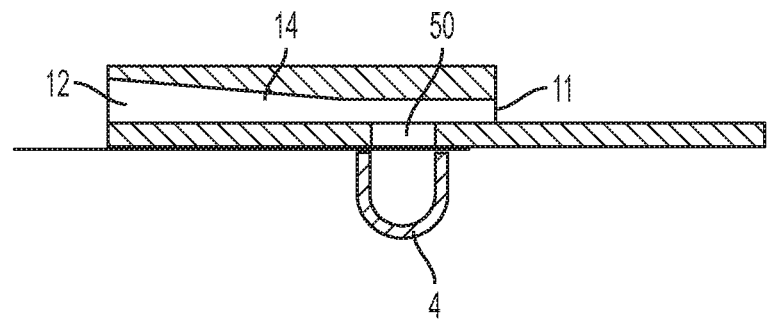
FIG. 21C shows a cross sectional side view of another alternative embodiment with air flow entering and exiting the dose chamber through a single opening.
Figure 21D:
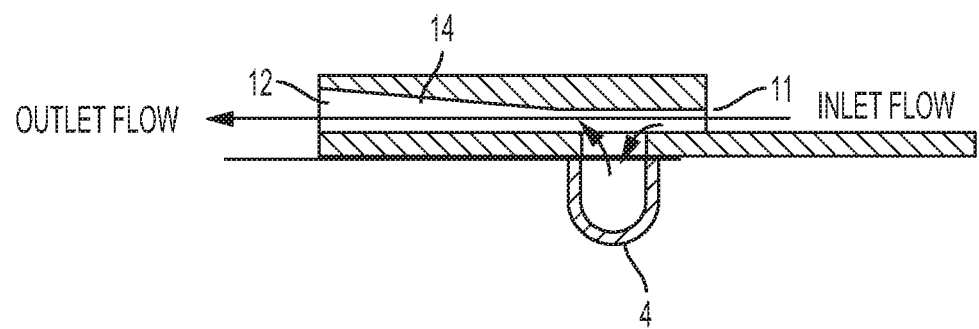
FIG. 21D shows a cross sectional side schematic view of the air flow in the FIG. 21C embodiment.

FIG. 21C shows a variation of the FIG. 21A embodiment in which the inlet opening 42 and the outlet opening 43 are combined into a single opening 50 and arranged in the flow path 14. Flow in the dose chamber 4 of the FIG. 21C embodiment is shown in FIG. 21D. Flow enters the dose chamber 4 via the single opening 50 and circulates back upwardly toward the flow path 14.

Figure 22A:
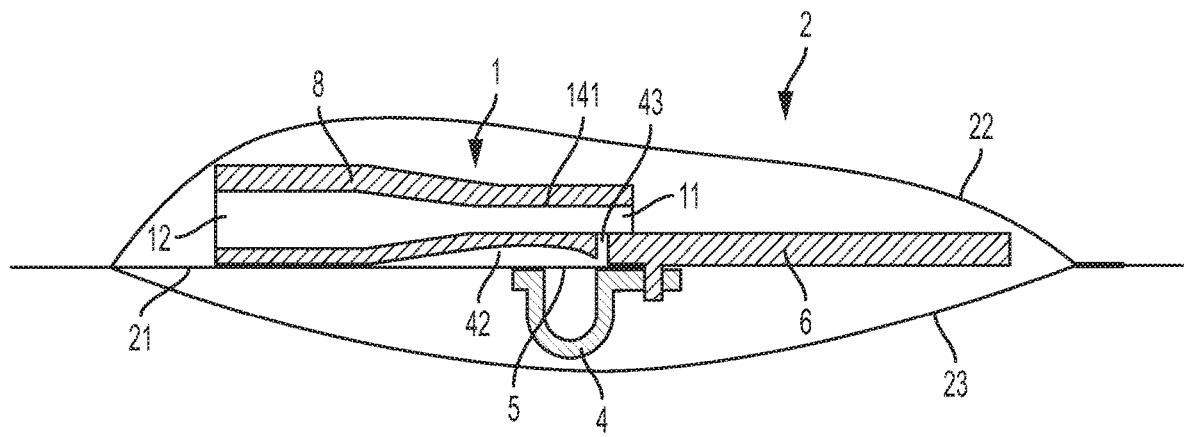
FIG. 22A shows a cross sectional side view of an alternative embodiment with air entering the dose chamber from outside of the flow path and crossing air flow in the dose chamber.
Figure 22B:
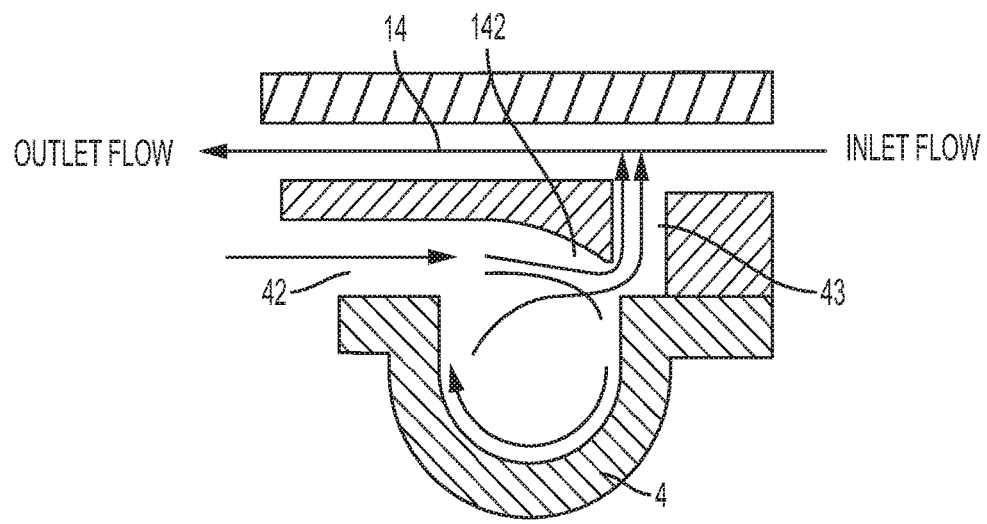
FIG. 22B shows a cross sectional side schematic of the air flow in the FIG. 22A embodiment.
Figure 22C:
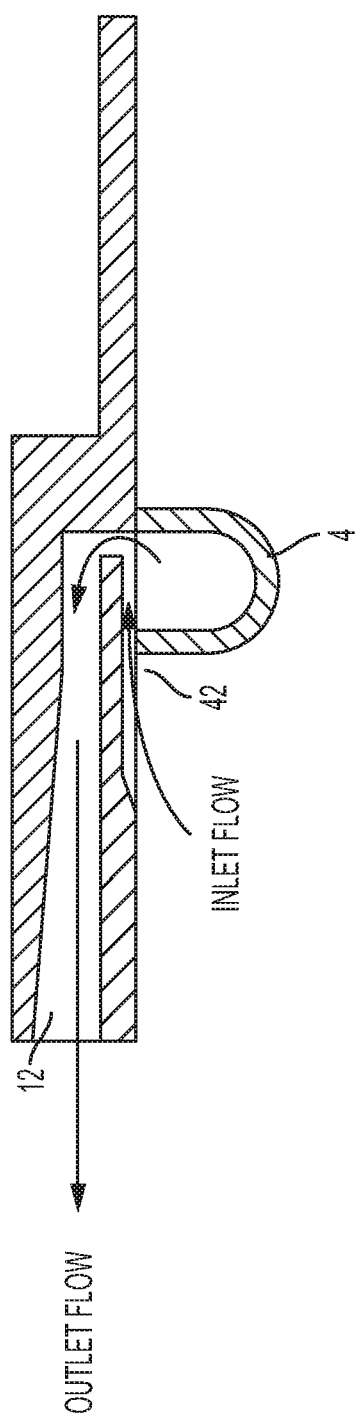
FIG. 22C shows a cross section side view of a further alternative embodiment with air entering through a single inlet opening from outside the flow path.
Figure 23A:
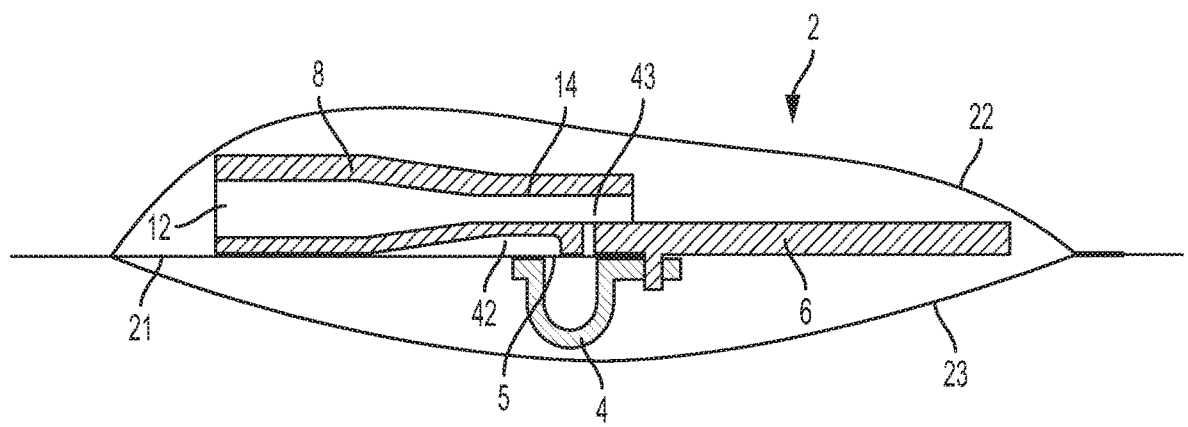
FIG. 23A shows a cross sectional side view of an alternative embodiment with air entering the dose chamber from outside of the flow path and flow in the dose chamber following a U shaped path.
Figure 23B:
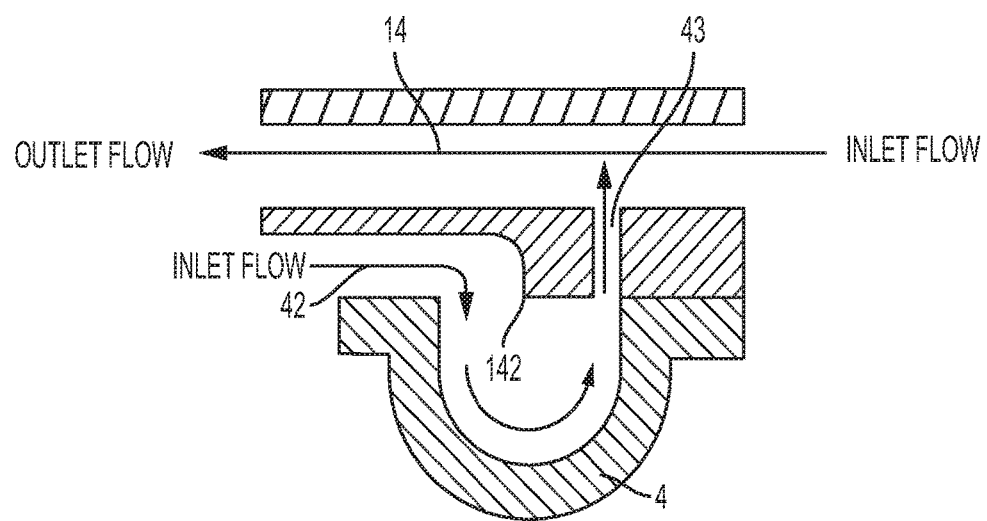
FIG. 23B shows a cross sectional side schematic of the air flow in the FIG. 23A embodiment.
Figure 24A:
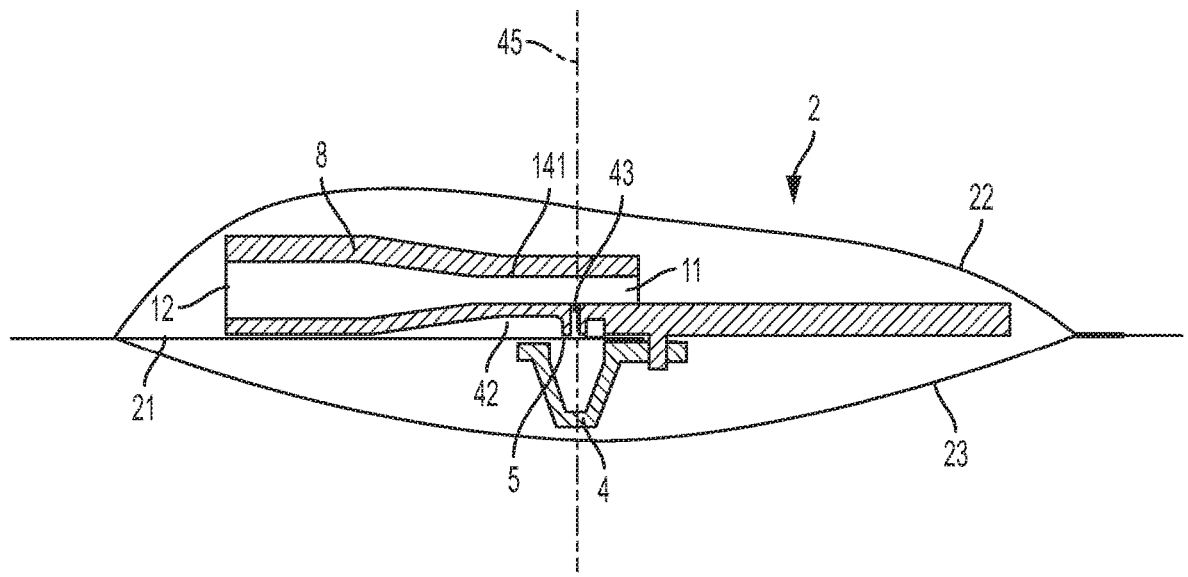
FIG. 24A shows a cross sectional side view of an alternative embodiment with a cyclone-type air flow in the dose chamber.
Figure 24B:
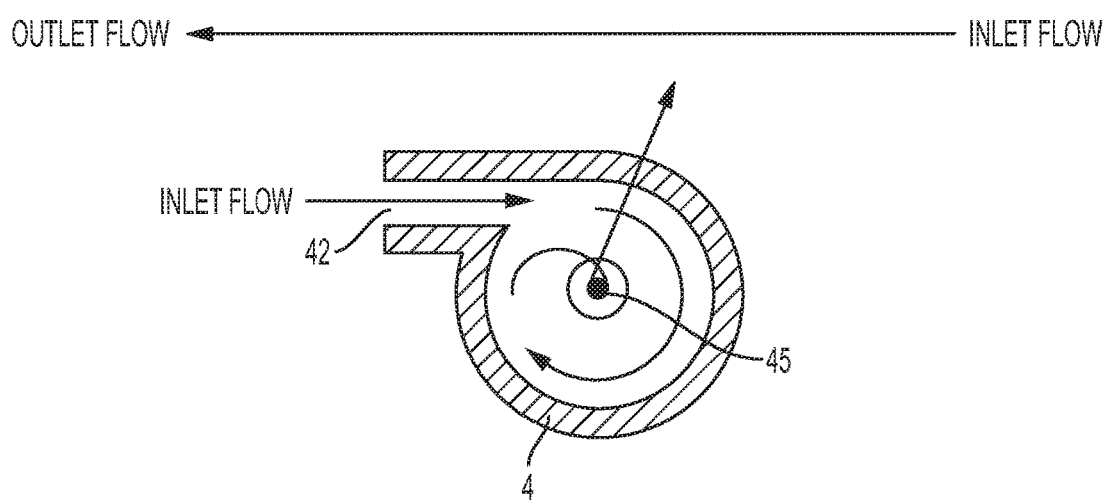
FIG. 24B shows a cross sectional side schematic of the air flow in the FIG. 24A embodiment.
Figure 25A:
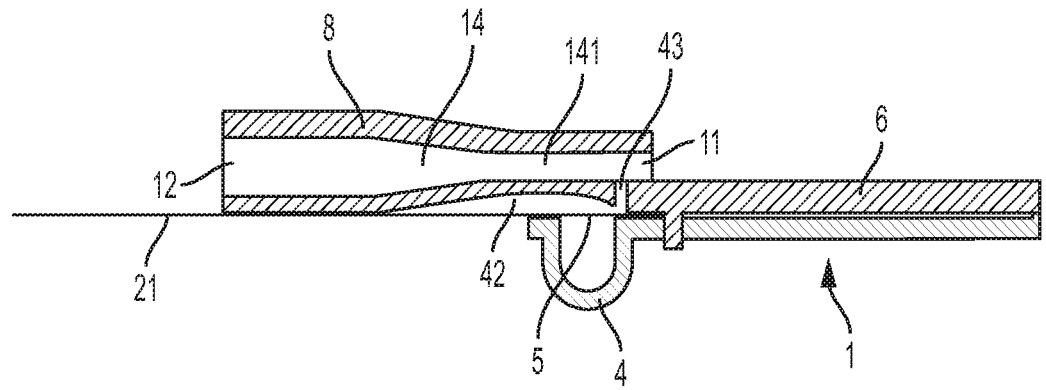
FIG. 25A shows a cross sectional side view of an alternative embodiment in its stored state including a living hinge.
Figure 25B:
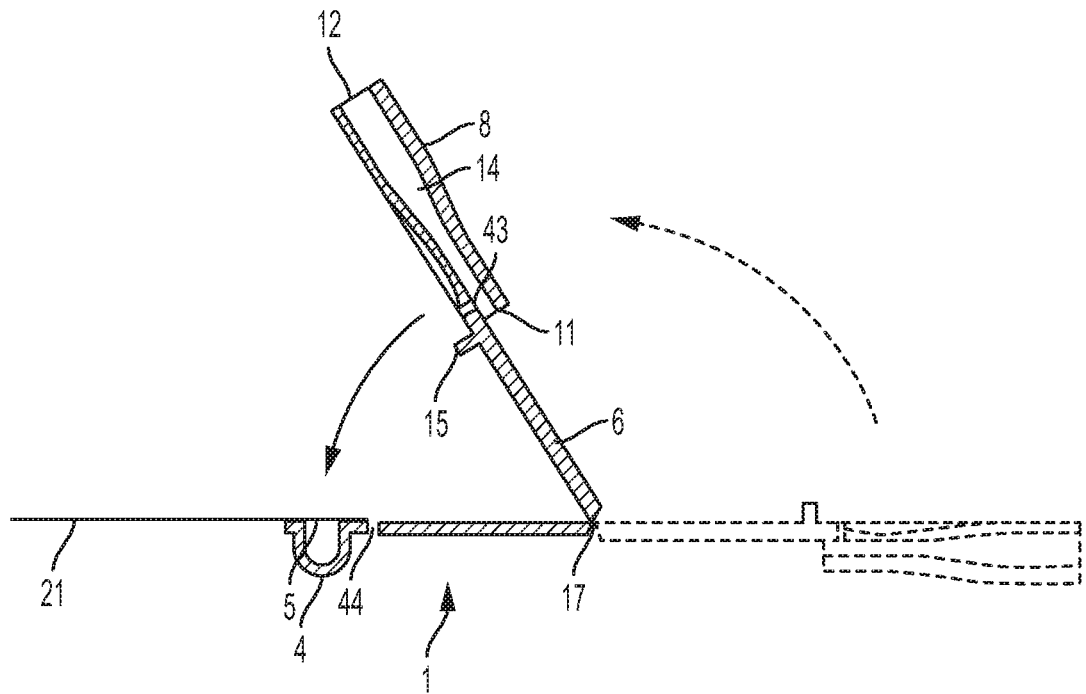
FIG. 25B shows a cross sectional side schematic of the living hinge folding in the FIG. 25A embodiment.

FIG. 22A shows another embodiment in which the inlet opening 42 is arranged outside of the flow path 14 and the outlet opening 43 is arranged in the flow path 14. As with the FIG. 1 embodiment, the inlet opening 42 is defined by both the body 1 and the dose chamber 4, whereas the outlet opening 43 is defined by the body 1. Flow in the dose chamber 4 is shown in FIG. 22B. Flow enters the dose chamber 4 via the inlet opening 42 in a direction along the direction of flow in the flow path 14, although in an opposite direction. The incoming flow is deflected downwardly by an obstacle 142 toward a bottom of the dose chamber 4 and circulates back upwardly toward the incoming flow. The recirculating flow crosses through the incoming flow and exits the dose chamber upwardly from via the outlet opening 43. Some of the incoming flow is able to pass directly to the outlet opening 43 without circulating in the dose chamber 4.

FIG. 22C shows a flow path variation of the FIG. 22B embodiment in which all of the incoming flow passes through the dose chamber 4 through inlet opening 42. This flow path arrangement locates the outlet 12 and inlet opening 42 in close proximity to facilitate covering of both openings by a cover.

FIG. 23A and FIG. 23B show yet another embodiment that is similar to that in FIG. 22A. However, in this embodiment, the obstacle 142 is positioned closer to the inlet opening 42 than the FIG. 22A embodiment such that incoming flow is deflected downwardly along a wall of the dose chamber adjacent the inlet opening 42 and follows a U-shaped path to the outlet opening 43. Thus, in this embodiment, flow in the dose chamber 4 does not recirculate, but rather generally makes a single pass through the dose chamber 4.

FIG. 24A shows another embodiment that includes a cyclone-type dose chamber 4. That is, in this embodiment, flow entering the dose chamber at the inlet opening 42 circulates about a vertical axis 45 that passes through the outlet opening 43. Circulation of the flow around the dose chamber 4 causes the dose to break into small particles, as needed, such that air exiting via the outlet opening 43 contains relatively small dose particles. Other larger particles are forced to move around the wall of the dose chamber 4 by centrifugal forces, until the particles break down sufficiently to exit the dose chamber 4. FIG. 24B shows a top view of the dose chamber 4 and how the inlet opening 42 is arranged to direct incoming flow along a side wall of the dose chamber 4, e.g., in a direction generally tangent to the sidewall at the point of entry.

FIGS. 25A and 25B show another embodiment in which the body 1 and dose chamber 4 may be made as a single part, e.g., molded of plastic as a single, unitary piece. Initially, the body 1 and dose chamber 4 may have a flat configuration, as suggested in FIG. 25B, i.e., the portion of the body 1 shown in dashed line may extend away from the body 1 portion including the dose chamber 4. To assemble the device 10, a seal 5 (and optional tab 21) may be positioned over the dose chamber 4 as shown in FIG. 25B. The seal 5 may be adhered or otherwise attached to the dose chamber 4 at this stage, or the seal 5 may simply be positioned over the dose chamber 4. The body 1 may be folded at a hinge 17 so that a protrusion 15 is received in an opening 44 as shown in FIG. 25A. The protrusion 15 may engage the opening 44 by interference fit, welding, adhesive, etc., and the engagement may clamp the seal 5 between the body 1 and the dose chamber 4 (or not, e.g., where the seal is attached to the dose chamber 4). Thereafter, the seal 5 may be attached to a cover 2 (not shown) and arranged to be removed from its sealing position with removal of the cover from a portion of the device 10.

In some embodiments, the device 10 may be arranged to carry information that can identify one or more of the device components so that the information can be used to determine characteristics of those components. For example, the device 10 could carry indicia, whether in the form of printed alphanumeric text, a barcode, an encoded magnetic strip, an RFID tag or other data element, a computer chip, etc., that can be used to identify one or more components of the device. The indicia may be used to determine when the device was made, what type and/or amount of dose is contained in the device, an intended user and/or use of the device, intended countries or other jurisdictions in which the device is authorized or otherwise available for use, and other. Indicia can also be used to track/encourage compliance with taking the medication. Thus, the indicia could be read from the device 10 (e.g., using a suitable RFID interrogator or reader) and used to determine the desired information. The indicia could include the desired information, such as the manufacture date, or could be used to retrieve such information from another source, such as a database associated with a suitable Internet website. Indicia, such as printed instructions, manufacturing information, instructions for opening the device, etc., may be provided on a cover 2.

According to some embodiments, a layer of barrier material or other cover 2 may include an aluminum foil that is substantially impervious to light and moisture, although in other embodiments, barriers may be permeable to some degree of moisture and light. The barrier may be readily adhered to other barriers, such as for foil-on-foil embodiments, or to other structures of a delivery device, that may be formed of plastic. Adhesives, heat weld, friction welds, and other fastening techniques may be used to affix barriers and to provide a seal between the barrier and mating structure.

It is to be appreciated that although various embodiments of the delivery devices are discussed and illustrated herein as a single dose device, that a plurality of any of the dose chambers may be incorporated into a device that may deliver multiple doses. Incorporating multiple dose chambers into a common device may allow some features of a delivery device to be shared among different dose chambers. By way of example, a multi-dose device may include a common outlet that is used to deliver, sequentially, doses from each of the dose chambers to a subject, when needed. Other features may be shared among the different dose chambers of a common, multi-dose device, such as a single actuation button and/or punch that is moved sequentially into registration with each dose chamber to move an opening mechanism between a first and second position to ready a dose for delivery, or a cassette is moved into registration with the punch. Additionally or alternatively, a multi-dose configuration may reduce the overall cost per dose to be delivered from a delivery device.

It is to be appreciated that the embodiments illustrated herein are merely representative embodiments of the various inventions, and that modifications may be made without departing from the spirit of the invention. By way of example, air pathways may be modified to have different shapes or features, or be located in various different parts of the dose deliver device for manufacturing or other reasons.

In some embodiments, the devices, systems and methods may be free of secondary packaging, i.e., packaging in addition to a cover, to facilitate rapid and easy delivery of the drug when the drug needs to be delivered as fast as possible under a stressful circumstance, such as in an emergency situation. However, some embodiments may have the entire device enclosed in a secondary closure, e.g., a bag of barrier layer foil or other material, to help preserve the dose 41 or otherwise provide the dose 41 with suitable conditions for storage.

Embodiments described herein may be configured for passive or active applications, or a combination of passive and active fluid administration. For example, each of the embodiments described herein may include use of a compressed fluid to assist in dispersing the drug.

The devices and systems described herein may be integrated into a wide variety of delivery configurations including, for example, a single-dose and multi-dose applications, in either active, passive, or active/passive applications. In addition, the devices, systems and methods may be applied to combination dose configurations and therapies.

The devices, systems and methods described herein may be used to deliver materials, other than a drug/medicament, to the body. The materials may be delivered through the mouth and/or nose and into the oral cavity, nasal cavity, and/or to the lungs. Materials that are intended to be delivered into the oral cavity include, for example, nutritional compositions (such as sugars, candy, food, vitamins, and quick energy supplements in liquid and/or powder (e.g., nanoparticles) form) and non-nutritional compositions (such as flavorants (e.g., esters)). Other materials that may be delivered into the oral cavity include those used for oral hygiene and dental treatment (e.g., breath fresheners, fluoride treatments, teeth whiteners, antibacterial compositions, mouthwashes). Drugs and related compositions (such as anesthetics, therapeutic markers) may also be delivered into the oral cavity. Materials that the may be inhaled into the lungs include, for example, drugs (e.g., for treating asthma, bronchitis, diabetes, pneumonia) and therapeutic markers (such as dyes, scanning agents, radio labeling or tagging agents, UV labeling agents, contrasts agents in liquid and/or powder (e.g., nanoparticles) form). In this respect, it is to be appreciated that any of the above materials may be used in the devices, systems, and methods described herein in place of drug(s)/medicaments. It is also to be appreciated that the terms "drug" and "medicament" are used interchangeable herein, and include any of the foregoing compositions and any others, whether in powder, liquid or other form, that may be delivered to a human or animal for therapeutic, diagnostic, or other effect. In certain aspects, the delivery device is configured for use with other entranceways into a human or animal body, whether naturally formed or created otherwise, and with aspects of the human or animal body other than the respiratory system. Although the embodiments described incorporate air as the fluid for delivering the medicament, other fluids are contemplated as should be apparent to one of skill in the art.

Although embodiments are described as including a "mouthpiece," it should be understood that a "mouthpiece" as used herein refers to an element that is downstream of a dose chamber and is intended to deliver an air/dose combination toward an ultimate outlet located at or near a user's mouth, nose or other receiving area. Thus, a "mouthpiece" need not necessarily be intended for contact with a human mouth. For example, a mouthpiece may be intended for use near a mouth, such as where a user holds the device spaced from the mouth and inhales dose/air emitted from the device outlet. In this situation (and others) the dose could potentially be delivered by squeezing a flexible dose chamber or other flexible portions of the housing and the resulting compressed air pushes the dose out to the user. In another embodiment, a mouthpiece may be intended for use with another element that is engaged with the mouthpiece (e.g., at the mouthpiece outlet 12) and is intended for contact with the user's mouth. In one example, a disposable or reusable sleeve or other conduit may be connected to the mouthpiece outlet 12 and provide an extension of the air path of the device beyond the mouthpiece outlet 12. The fact that a dose delivery device is used, or intended for use, with such a sleeve would not render the air flow component downstream of the dose chamber (i.e., the "mouthpiece") that conducts an air/dose combination not a "mouthpiece" as used herein.

While the principles of the invention have been described herein, it is to be understood by those skilled in the art that this description is made only by way of example and not as a limitation as to the scope of the invention. Other embodiments are contemplated within the scope of the present invention in addition to the exemplary embodiments shown and described herein. Modifications and substitutions by one of ordinary skill in the art are considered to be within the scope of the present invention, which is not to be limited except by the following claims.

What is claimed is:

1. A dose delivery device, comprising:
    a body including a mouthpiece having an outlet, the body defining a flow path extending from an inlet to the outlet;
    a dose chamber containing a dose to be delivered to a subject via the mouthpiece;
    a seal that closes fluid communication between the flow path and the dose chamber; and a cover that completely surrounds the body and the dose chamber, the cover including at least one barrier layer, wherein the cover is connected to the seal such that separation of the cover from the body and the dose chamber causes the seal to open fluid communication between the flow path and the dose chamber, wherein the seal includes a wall that is slidably engaged with the body and configured to be guided in linear movement relative to the body across an opening of the dose chamber when moved from a closed position to an open position upon removal of the cover.

2. The device of claim 1, wherein a portion of the at least one barrier layer near the mouthpiece outlet is attached to a tab that extends to the seal.

3. The device of claim 1, wherein the body includes a handle arranged for gripping by a user to support the device during use.

4. The device of claim 3, wherein the handle extends away from the mouthpiece in a direction along the flow path.

5. The device of claim 1, wherein the cover includes a pair of barrier layers, a first layer of the pair of barrier layers forming a blister in which the body and the dose chamber are positionable, and a second layer of the pair of barrier layers sealed to the first layer to enclose the blister.

6. The device of claim 5, wherein the dose chamber has a spoon shape and is arranged to engage the body at a handle portion of the spoon shape.

7. The device of claim 1, wherein the dose chamber defines two separate spaces in which dose is located and is deliverable to the flow path.

8. The device of claim 1, wherein the seal includes a portion that extends along an outer surface of the mouthpiece to a position near the dose chamber.

9. The device of claim 1, wherein the body and the dose chamber define an inlet opening to the dose chamber and an outlet opening from the dose chamber to the flow path.

10. The device of claim 1, wherein the dose chamber is arranged such that air flow into the dose chamber circulates in the dose chamber to entrain dose.

11. The device of claim 1, wherein the dose chamber and the body are arranged such that dose-entrained air flowing from the dose chamber to the flow path enters the flow path in a direction perpendicular to flow in the flow path.

12. The device of claim 1, wherein the dose chamber and the body are arranged such that dose-entrained air flowing from the dose chamber to the flow path enters the flow path at a restriction in the flow path.

13. The device of claim 1, wherein flow in the flow path is along an axis from the inlet to the outlet.

* * * * *